(12) United States Patent
Patel et al.

(10) Patent No.: US 11,903,562 B2
(45) Date of Patent: Feb. 20, 2024

(54) ENCASEMENT PLATFORM FOR SMARTDEVICE FOR ATTACHMENT TO ENDOSCOPE

(71) Applicant: Endoluxe Inc., North Brunswick, NJ (US)

(72) Inventors: Neal Patel, North Brunswick, NJ (US); Philip Zhao, Fort Lee, NJ (US)

(73) Assignee: Endoluxe Inc., Dunwoody, GA (US)

( * ) Notice: Subject to any disclaimer, the term of this patent is extended or adjusted under 35 U.S.C. 154(b) by 1215 days.

(21) Appl. No.: 16/189,181

(22) Filed: Nov. 13, 2018

(65) Prior Publication Data

US 2019/0133424 A1 May 9, 2019

Related U.S. Application Data

(63) Continuation of application No. 14/737,766, filed on Jun. 12, 2015, now Pat. No. 10,130,244.

(Continued)

(51) Int. Cl.
*A61B 1/04* (2006.01)
*G03B 17/56* (2021.01)
(Continued)

(52) U.S. Cl.
CPC ............ *A61B 1/04* (2013.01); *A61B 1/00052* (2013.01); *A61B 1/00124* (2013.01); *A61B 1/06* (2013.01); *A61B 1/0661* (2013.01); *A61B 1/0669* (2013.01); *A61B 5/6898* (2013.01); *A61B 18/04* (2013.01); *G03B 17/48* (2013.01); *G03B 17/565* (2013.01); *H04M 1/724092* (2022.02); *A61B 2018/00172* (2013.01); *A61B 2018/00178* (2013.01); *A61B 2218/002* (2013.01); *A61B 2218/007* (2013.01); *A61B 2560/045* (2013.01); *A61B 2562/225* (2013.01); *A61M 16/01* (2013.01); *A61M 2202/0208* (2013.01);

(Continued)

(58) Field of Classification Search
CPC .... A61B 1/0669; A61B 1/0661; A61B 5/6898
See application file for complete search history.

(56) References Cited

U.S. PATENT DOCUMENTS 4,478,212 A 10/1984 Asano
5,822,546 A 10/1998 George
(Continued)

OTHER PUBLICATIONS

NPL 1 [Nova Is A Wireless External Flash For iPhone To Take Better-Looking Low Light Shots, Hardware 2013] (Year: 2013).*

(Continued)

*Primary Examiner* — Oommen Jacob
(74) *Attorney, Agent, or Firm* — Dentons US LLP

(57) ABSTRACT

A case or encasement for use with a smartdevice, such as a smartphone or tablet and an endoscope is disclosed. The encasement includes a power supply, logic for controlling wireless communications, a light source, and other accessories, for use with an endoscope. In an embodiment, the encasement includes a power supply that may be used to charge a smartdevice, power a light source and a wireless communications module. Other embodiments include a mechanism for communicating between the smartdevice and the encasement to control the light source and any other accessories coupled to the encasement.

20 Claims, 16 Drawing Sheets

Related U.S. Application Data

(60) Provisional application No. 62/011,171, filed on Jun. 12, 2014.

(51) Int. Cl.

| | | |
|---|---|---|
| *A61B 1/00* | (2006.01) | |
| *A61B 5/00* | (2006.01) | |
| *A61B 1/06* | (2006.01) | |
| *G03B 17/48* | (2021.01) | |
| *A61B 18/04* | (2006.01) | |
| *H04M 1/72409* | (2021.01) | |
| *A61M 16/01* | (2006.01) | |
| *A61B 18/00* | (2006.01) | |
| *H04M 1/02* | (2006.01) | |
| *H04M 1/04* | (2006.01) | |
| *H04M 1/72412* | (2021.01) | |

(52) U.S. Cl.
CPC .......... *A61M 2205/505* (2013.01); *A61M 2205/8206* (2013.01); *H04M 1/0264* (2013.01); *H04M 1/04* (2013.01); *H04M 1/72412* (2021.01)

(56) References Cited

U.S. PATENT DOCUMENTS

| | | | |
|---|---|---|---|
| 6,646,866 | B2 | 11/2003 | Kao |
| 6,657,654 | B2 | 12/2003 | Narayanaswami |
| 7,986,342 | B2 | 7/2011 | Yogesan et al. |
| 8,604,753 | B2 | 12/2013 | Bessa et al. |
| 8,711,552 | B2 | 4/2014 | Medica et al. |
| D710,856 | S | 8/2014 | Daniel |
| 8,928,746 | B1 | 1/2015 | Stevrin et al. |
| 8,944,596 | B2 | 2/2015 | Wood et al. |
| 10,457,441 | B2 * | 10/2019 | O'Neill .................. H04M 1/04 |
| 2002/0103420 | A1 | 8/2002 | Coleman et al. |
| 2003/0050534 | A1 | 3/2003 | Kazakevich |
| 2003/0227746 | A1 | 12/2003 | Sato |
| 2006/0116550 | A1 | 6/2006 | Noguchi et al. |
| 2006/0215013 | A1 | 9/2006 | Jongsma et al. |
| 2008/0104300 | A1 | 5/2008 | Diener et al. |
| 2008/0183910 | A1 | 7/2008 | Natoli et al. |
| 2008/0207996 | A1 * | 8/2008 | Tsai .................. G02B 23/2407 |
| | | | 600/112 |
| 2009/0186264 | A1 | 7/2009 | Huang |
| 2010/0198009 | A1 | 8/2010 | Farr et al. |
| 2010/0279418 | A1 | 11/2010 | Larson et al. |
| 2011/0015496 | A1 | 1/2011 | Sherman et al. |
| 2011/0050164 | A1 * | 3/2011 | Partovi .................. H02J 50/90 |
| | | | 320/108 |
| 2011/0055447 | A1 | 3/2011 | Costa |
| 2011/0195753 | A1 * | 8/2011 | Mock .................. H04B 1/3888 |
| | | | 455/566 |
| 2012/0077552 | A1 | 3/2012 | Bessa et al. |
| 2012/0106037 | A1 | 5/2012 | Diebel et al. |
| 2012/0162401 | A1 | 6/2012 | Melder et al. |
| 2012/0225622 | A1 | 9/2012 | Kudrna et al. |
| 2012/0320340 | A1 * | 12/2012 | Coleman, III ........... A61B 3/10 |
| | | | 351/208 |
| 2013/0083185 | A1 | 4/2013 | Coleman |
| 2013/0096378 | A1 | 4/2013 | Alexander et al. |
| 2013/0102359 | A1 * | 4/2013 | Ho .......................... H04M 1/21 |
| | | | 455/556.1 |
| 2013/0177304 | A1 * | 7/2013 | Chapman ............. G03B 17/565 |
| | | | 396/533 |
| 2013/0262730 | A1 | 10/2013 | Al-Ali et al. |
| 2013/0281155 | A1 | 10/2013 | Ogata et al. |
| 2013/0344917 | A1 | 12/2013 | Sobti et al. |
| 2014/0028243 | A1 * | 1/2014 | Rayner .................. H04N 5/2257 |
| | | | 320/108 |
| 2014/0038222 | A1 | 2/2014 | Alt et al. |
| 2014/0051923 | A1 * | 2/2014 | Mirza ................ A61B 1/00009 |
| | | | 600/103 |
| 2014/0073969 | A1 | 3/2014 | Zou et al. |
| 2014/0140049 | A1 | 5/2014 | Cotelo |
| 2014/0142390 | A1 * | 5/2014 | Bromwich ......... A61B 1/00131 |
| | | | 600/160 |
| 2014/0170761 | A1 | 6/2014 | Crawford et al. |
| 2014/0192492 | A1 * | 7/2014 | Wojcik .................... G06F 21/86 |
| | | | 361/752 |
| 2014/0200054 | A1 | 7/2014 | Fraden |
| 2014/0249405 | A1 | 9/2014 | Wimer |
| 2014/0364711 | A1 | 12/2014 | Ismail et al. |
| 2015/0002606 | A1 | 1/2015 | Hyde et al. |
| 2015/0073285 | A1 | 3/2015 | Albert et al. |
| 2015/0087926 | A1 * | 3/2015 | Raz ...................... A61B 5/0022 |
| | | | 600/301 |
| 2015/0227178 | A1 * | 8/2015 | Rayner ................... G06F 1/163 |
| | | | 361/679.02 |
| 2015/0254072 | A1 | 9/2015 | Wojcik et al. |
| 2015/0373180 | A1 * | 12/2015 | Kari ..................... G06F 1/1632 |
| | | | 455/556.1 |
| 2015/0381887 | A1 * | 12/2015 | Sato ..................... H04N 23/631 |
| | | | 348/207.11 |
| 2019/0133424 | A1 * | 5/2019 | Patel .................... A61B 1/0669 |

OTHER PUBLICATIONS

International Search Report and Written Opinion dated Sep. 18, 2015 in related PCT Application No. PCT/US15/35479 filed Jun. 12, 2015 (7 pages).

* cited by examiner

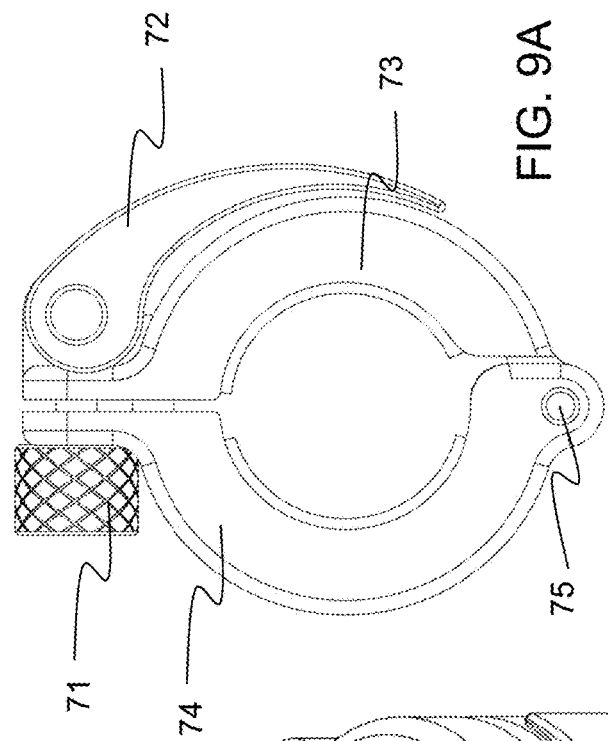
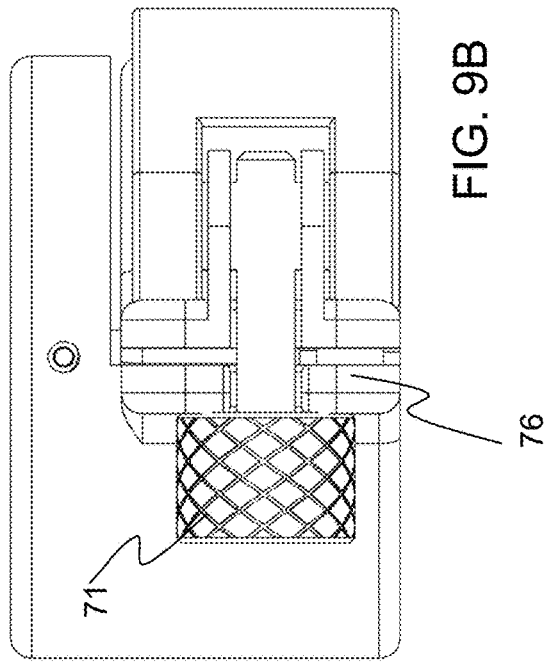
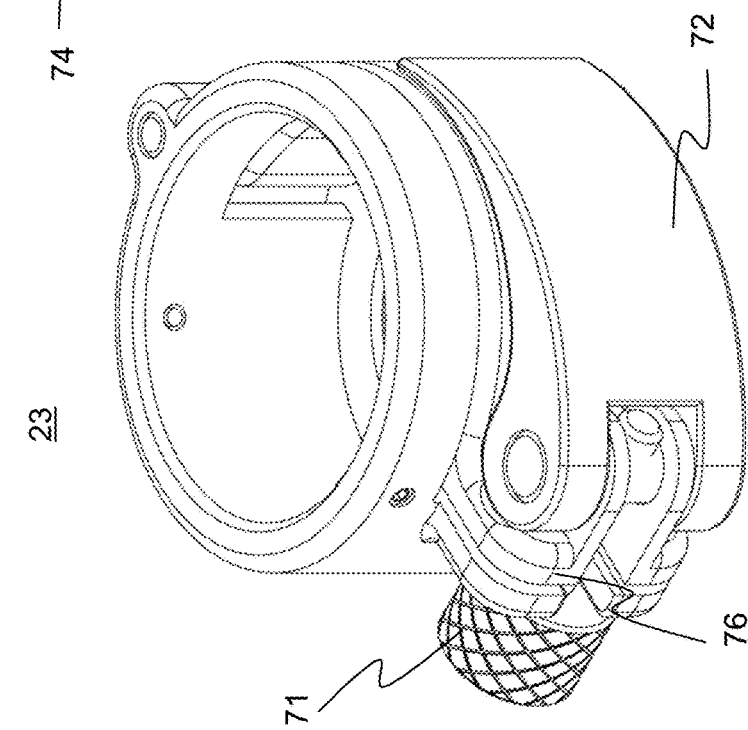

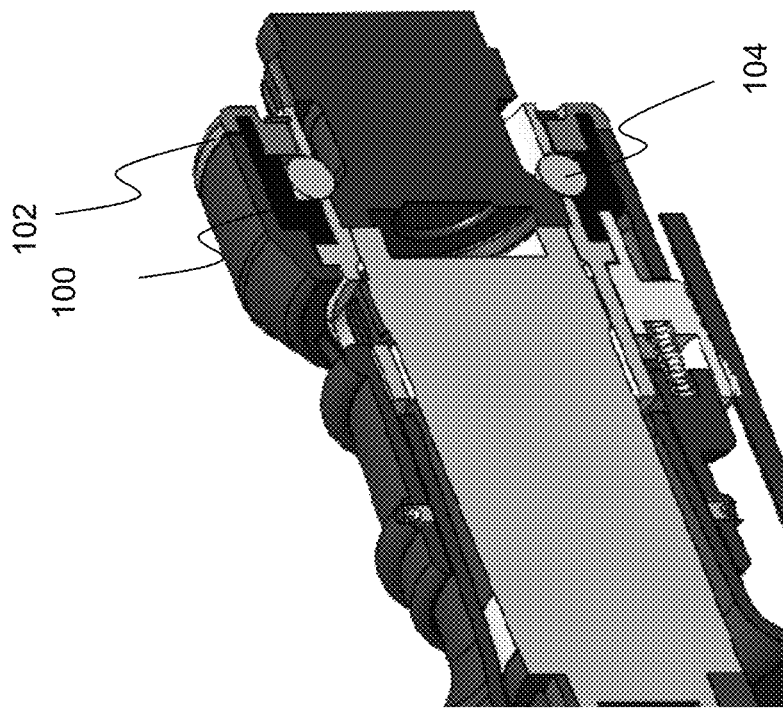
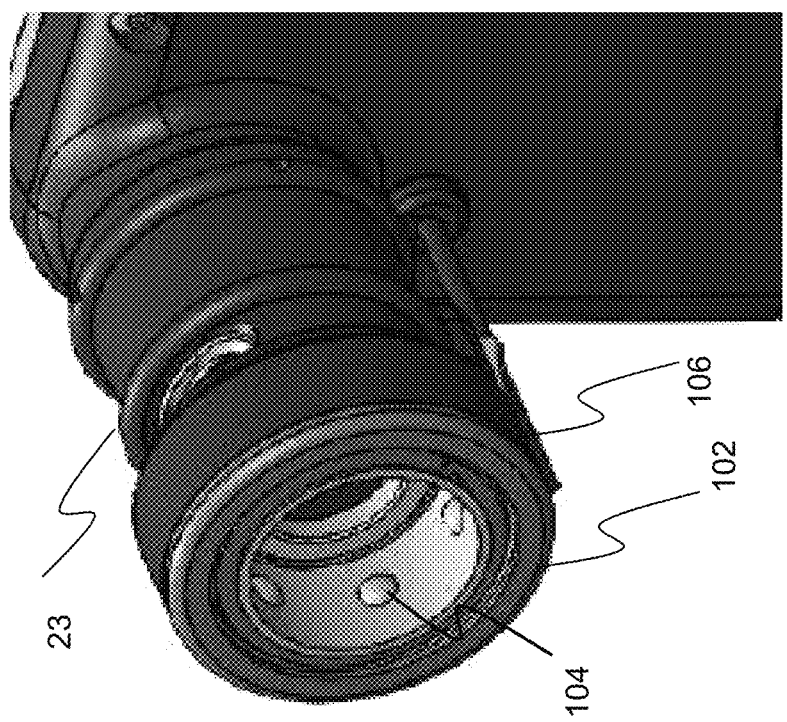
FIG. 10A
FIG. 10B

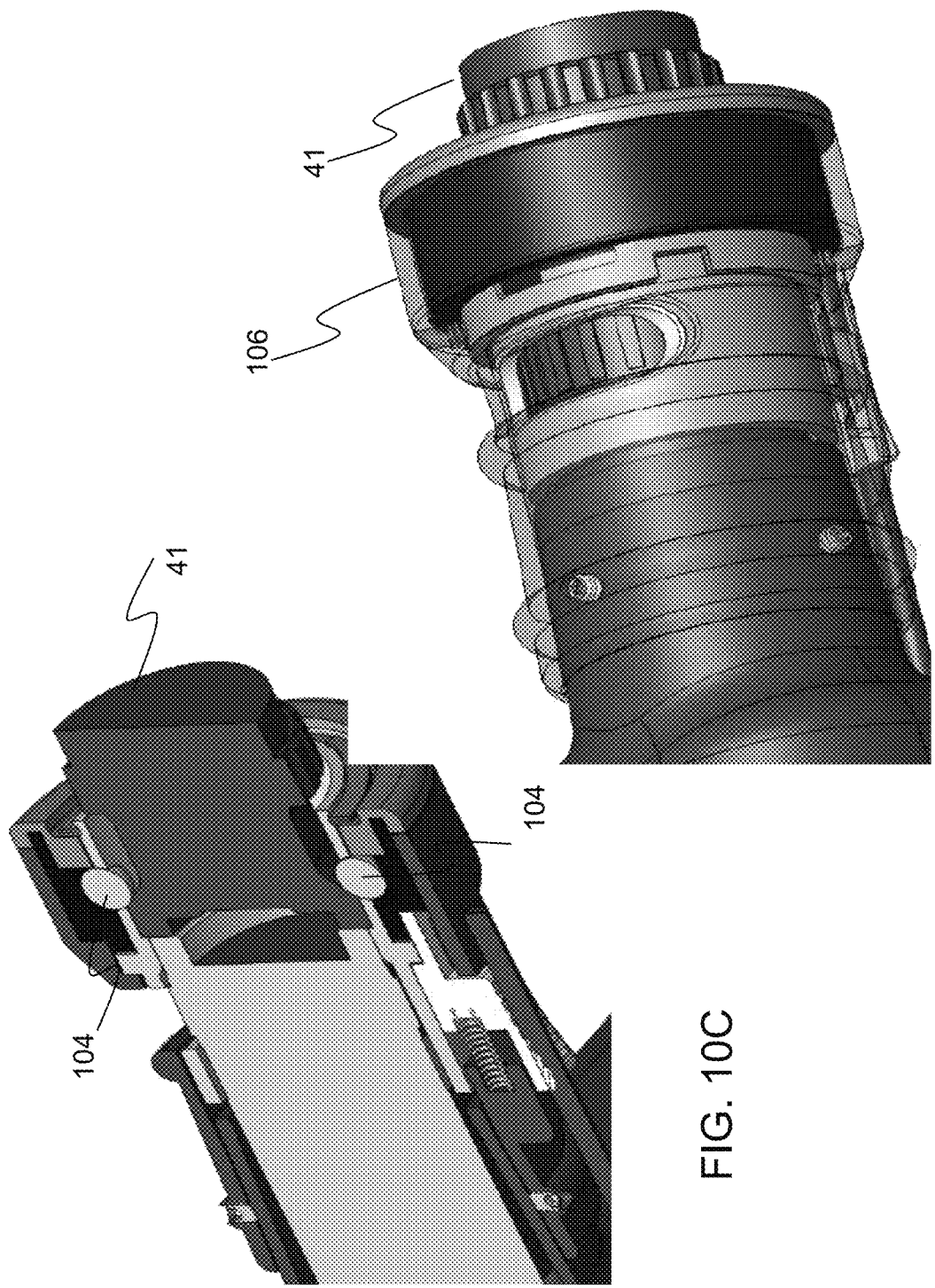

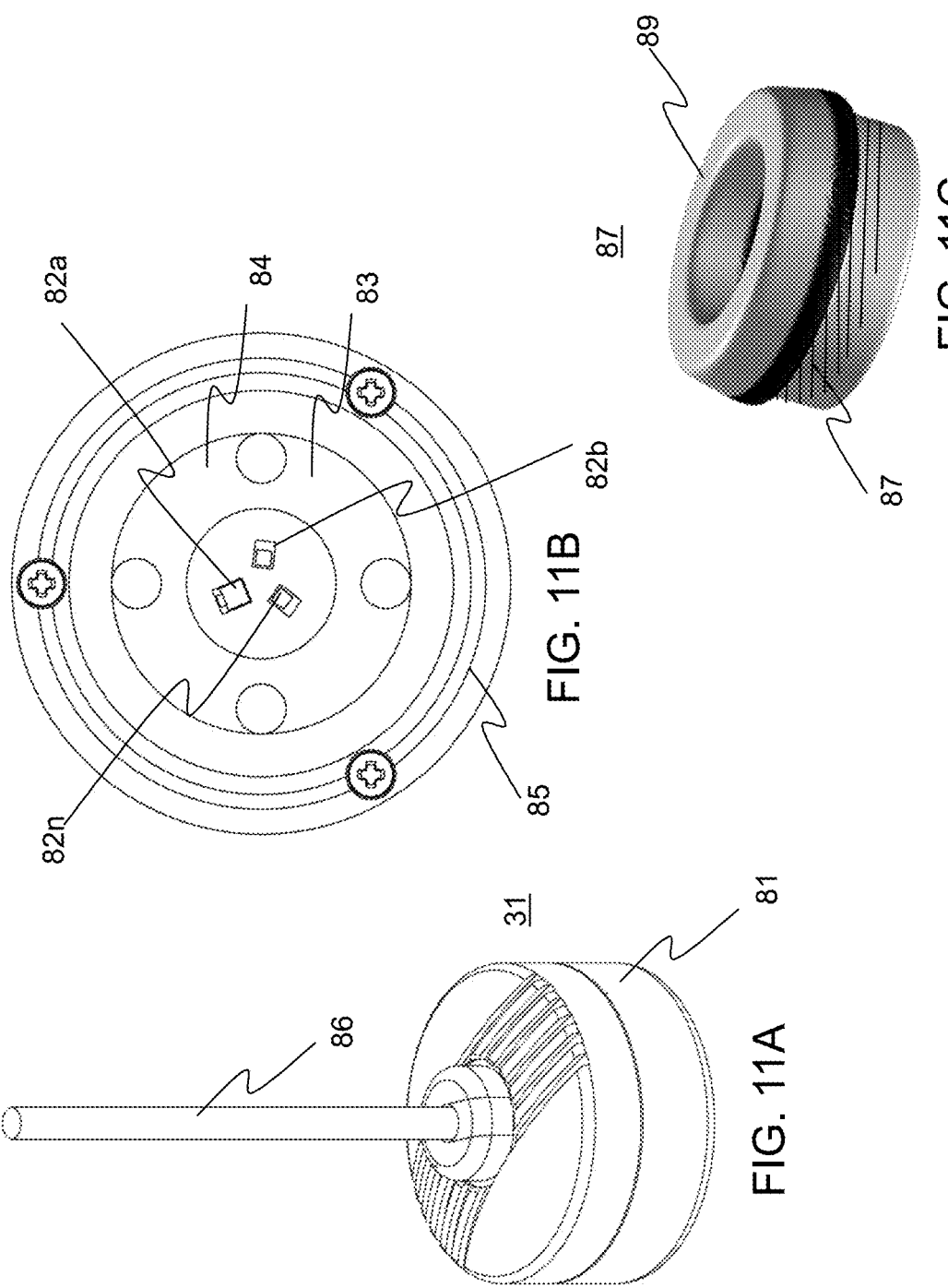

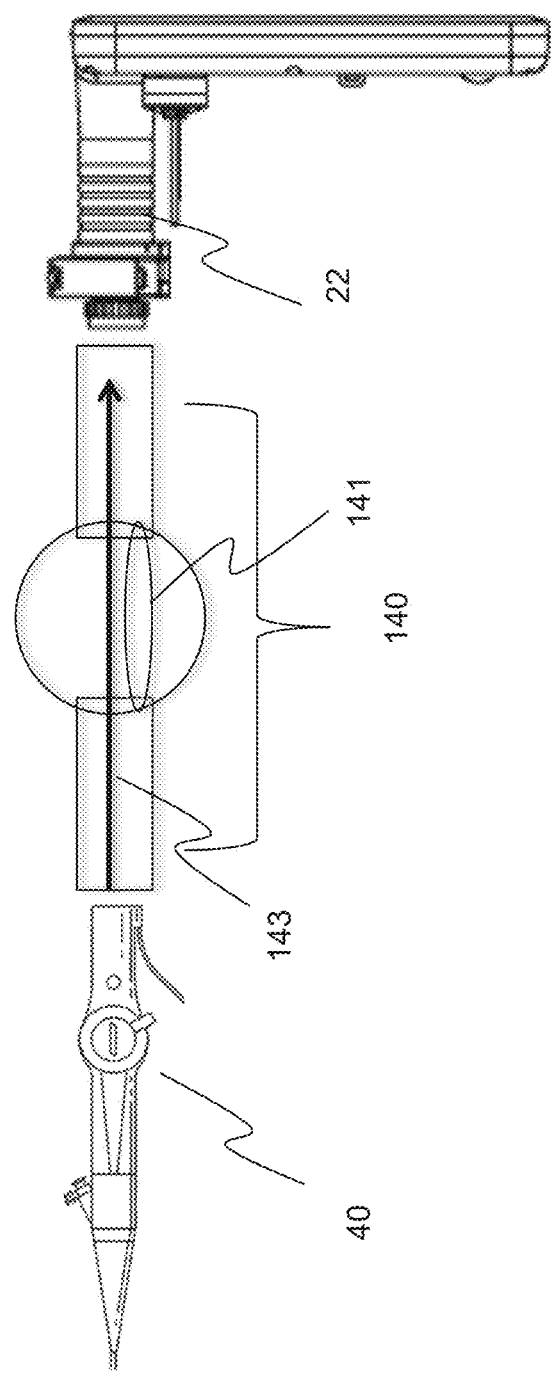

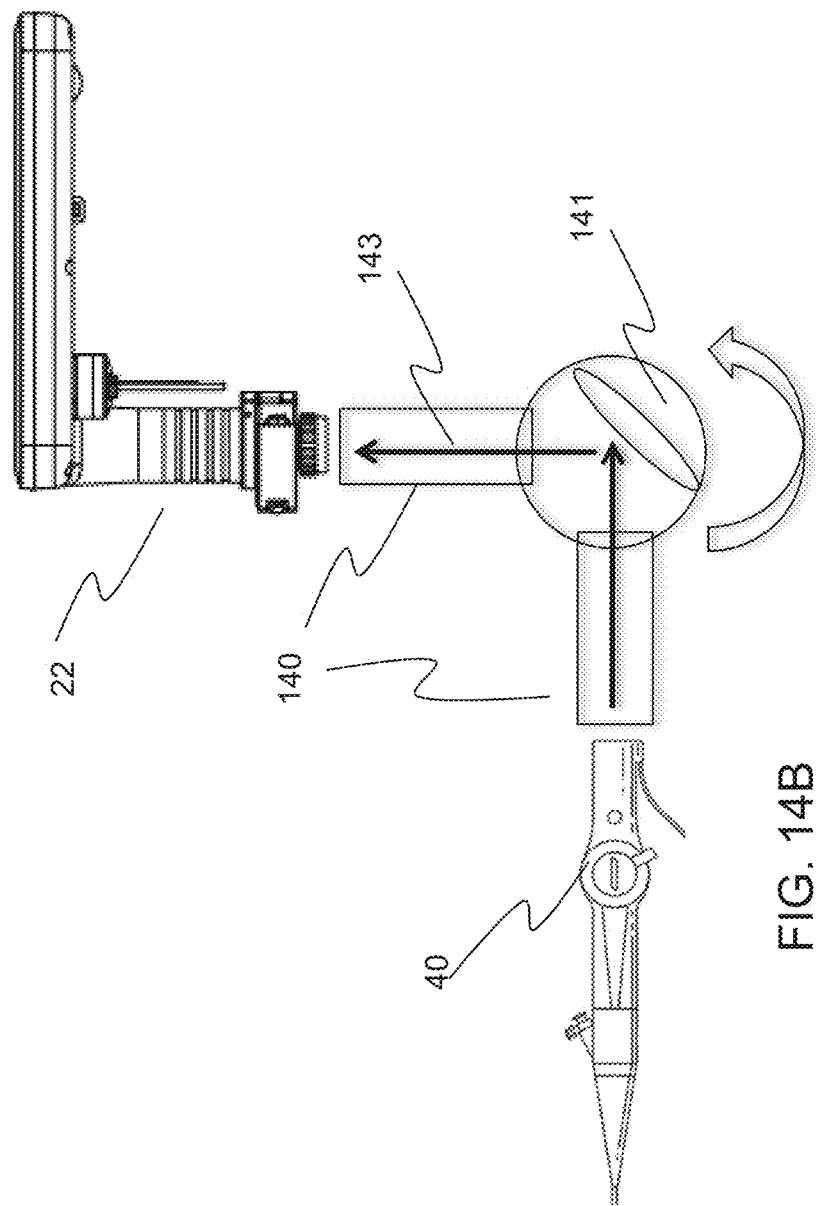

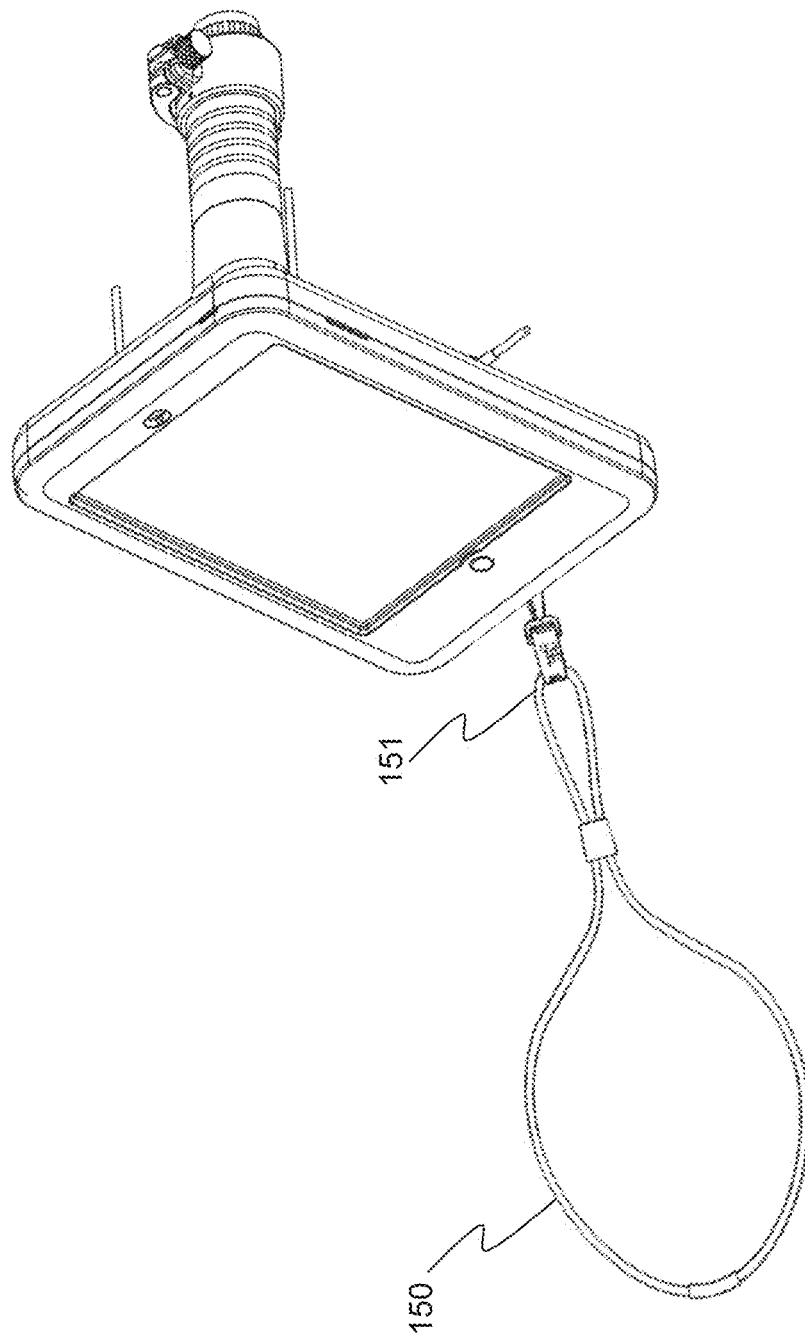

ENCASEMENT PLATFORM FOR SMARTDEVICE FOR ATTACHMENT TO ENDOSCOPE

CROSS REFERENCE TO RELATED APPLICATIONS

The present application is a Continuation of U.S. application Ser. No. 14/737,766 filed 12 Jun. 2015; which claims a benefit of priority to U.S. 62/011,171 filed 12 Jun. 2014, each of which is incorporated herein by reference in its entirety for all purposes.

TECHNICAL FIELD

This invention relates generally to an active encasement for a smartdevice and more particularly to a powered encasement with logic and communication circuitry to be used as part of an imaging system utilized during endoscopic procedures.

BACKGROUND

Endoscopic procedures are a mainstay of interventional medicine. The endoscope is a device comprising a lens, a flexible tube used to enter an orifice or narrow opening, that accepts a light source and can interface with an imaging system allowing personnel to examine a patient or an object in a minimally invasive manner and permitting observation and intervention within a body cavity or in an enclosed space. The original endoscope was invented in the early nineteenth century using a series of lens for magnification and a candle to produce light. The basic principle consists of using a tubular device with optics to traverse the natural bodily lumens to investigate and analyze the inner workings of the human body. These endoscopes can also be used for intervention (for example, introducing a biopsy forceps through the endoscope to remove tissues for biopsy; using electrocautery to destroy cancerous tissue; or using a tracheoscope to help intubate a patient and protect the airway, etc.). Endoscopes transmit an image from its distal end to an eyepiece at the proximal end, either directly or through an image-processing unit. It may then be magnified and viewed directly or displayed on a separate screen. The endoscope usually needs a light source to illuminate the area of investigation. Many endoscopes (for example, cystoscopy) need irrigation fluid to produce turbulence to clear away debris, distend a lumen for the endoscope to maneuver, and help improve visualization.

Endoscopes may be used in applications outside the field of medicine as well. For example, endoscopes may be used to inspect pipes, engines and other internal cavities. An endoscope can and has been used for purposes such a military/police personnel looking through a keyhole or under the door to evaluate a tactical situation, or a plumber evaluating pipes or where an obstruction has occur within an enclosed system through a small port hole.

Generally, endoscopic devices are expensive due to their specialized services and especially so in medicine due to the need for sterility in medical applications. Subsequent iterations have improved with advancement in lens production and technology. The modern flexible endoscope uses fiber optics for light transmission. The image is usually transmitted and processed through an expensive and complex image-processing unit that then displays the image on a separate video screen. This collection of images and video processing units and displays are usually bulky and not mobile, and thus not practical in emergent use or in areas of the world were such equipment are cost prohibitive. Furthermore, using an external video capture or screening device usually requires bulky monitors, external cabling and external power. Similarly, the typical endoscope light source is remote to the endoscope and must be connected via a fiber-optic type cable from a source to the light port of an endoscope. This limits the movement and mobility of the endoscope.

Accordingly, there is a need for an inexpensive, lightweight, mobile platform that is both accurate and reliable, and does not require an excessive amount of time to assemble or external connections or cables. The imaging system described herein may be used medically and for medical education during urology, gynecology, gastroenterology, anesthesia, otolaryngology, pulmonology, general/bariatric surgery, orthopedic surgery procedures and any other surgical or medical subspecialty that may utilize endoscopic technology. It can assist with and facilitate with telemedicine education as well as evaluation and interpretation of endoscopic procedures. This device relates to a mobile platform for enhancing visualization during endoscopic procedures utilizing standard smartdevices, such as tablet computers, in the medical and/or industrial field.

There is also a need for a device or system that is designed for operators who have variable skill levels and need what is visualized through the endoscope to be displayed, augmented and shown to other team members/instructors both local to the procedure and/or conveyed over a network to remote users/viewers in other locations. The present disclosure describes such a device.

BRIEF SUMMARY

In an embodiment, an encasement to house a smartdevice with a camera is disclosed. The encasement comprises a case, an endoscope mount with an endoscope clamp, an encasement power supply, encasement circuitry, and a communications interface.

In another embodiment, the encasement further comprises a peripheral device and or a connector for adding a peripheral device. In a further embodiment, the peripheral device is a high intensity lamp. In a further embodiment the peripheral device is powered by the encasement power supply. In another embodiment, the encasement power supply is a rechargeable battery. In still another embodiment, the encasement power supply charges a smartdevice.

In another embodiment the peripheral device is selected from one of the following, a peristaltic pump, a suction device, an irrigation device, a cauterizer, an insufflator, gas delivery device, vital measurement device, and fluid management system.

In another embodiment, the encasement communications interface receives communications from a smartdevice and controls the light source in response to the communications.

In another embodiment, the intensity and wavelength of light from the high intensity lamp may be varied. In another embodiment, the encasement case may be sterilized. In another embodiment, the encasement comprises an opening for receiving a smartdevice, and the endoscope clamp aligns, an endoscope with an eyepiece, with the camera of the smartdevice.

In another embodiment, an encasement for use in a handheld portable imaging system is described. The encasement for use in a handheld portable imaging system comprises an endoscope clamp, a light source, a power source, a communications interface; and a wireless controller, wherein the endoscope clamp is coupled to an endoscope with an eyepiece and the encasement, and aligns the endoscope eyepiece with a camera of a smartdevice such that an image viewed through the endoscope eyepiece is magnified and displayed on the smartdevice.

In another embodiment, the wavelength of light from the light source can be modified to project different light spectra for the purposes of disease detection within a tissue being examined. In another embodiment, the wavelength of light can be applied using the light source and the smartdevice can apply post-image processing through software without hardware filters, to augment and specify the image displayed.

In another embodiment, the encasement comprises a lens subassembly and the lens sub assembly can be rotated so the encasement and image lie perpendicular to the endoscope through the use of a mirror in a rotating hub of the lens assembly. In an embodiment, a harness can be attached to the encasement.

The apparatus can fit any smartdevice (such as, but not limited, to a smart phone or tablet computer). The embodiments described herein make reference to tablets computers, such as the Apple® iPad™ or iPad Mini™, but it should be understood that any tablet device, PDA, smart phone, hybrid laptop/tablet may be used in conjunction with the encasement described herein.

The encasement in an embodiment is a self-powered housing, that comprises a communications interface, power module and logic circuitry that holds a smartdevice and connects it to an endoscope with multiple venues of attachment to the device that augments a user's experience in performing endoscopic procedures. The present disclosure takes advantage of modern consumer electronics in combination with components of endoscopic systems to provide for a lower cost examination and intervention device. More specifically, the present disclosure makes use of a mobile smartdevice/computing device to provide a camera, image sensor, lens, a display and image processing software, and light source.

In an embodiment, the encasement platform has communication abilities (Bluetooth, Wi-Fi, direct connection) with the smartdevice. The smartdevice via its communications with the encasement is able to control all software functions of the device in all respects. In an embodiment, the encasement includes its own rechargeable battery power source to power both the smartdevice and the encasement, a self-contained light source (providing light in multiple spectrums) to supply light to the endoscope, and other attachments for various modules that can be used during endoscopy (e.g. peristaltic pump, suction mechanism). In an embodiment, the power source can be charged using direct current or through induction mechanisms.

In an embodiment, a clamping system attaching the encasement to an endoscope utilizes a simple single or two-clamp mechanisms to provide additional support of various endoscopic equipment and is able to fit a variety of sizes of endoscope eyepiece necks. It is to be understood that the clamping system for coupling the endoscope to the encasement can be a neck clamp, a press fit, a friction fit, or a magnetic fitting. In an embodiment, two-clamps are used to attach the encasement to the endoscope: All endoscopes have a universal eyepiece; most existing adapter clamps, clamp onto only the rim of the eyepiece without any connections or support of the neck of the endoscope. In an embodiment, the encasement utilizes an adjustable clamp that can clamp onto endoscope neck distal to the eyepiece at various thickness. In this way, additional support and security are provided to the overall clamping mechanism during operation and use.

In an embodiment, the encasement and the entire system is water-resistant and protects the smartdevice from damage during use. The encasement can be sterilized via any known sterilization technique and can also support the use of a sterile cover that can be attached to the entire system to provide additional sterility. In an embodiment, the encasement itself is waterproof and washable and creates a barrier, protecting the smartdevice from fluid contamination.

In an embodiment, a magnetic light adapter is used to couple a light source to the endoscope. The magnetic adapter can be attached to the light post guide of any endoscope. The light source is then magnetically attached to this adapter and can be easily installed and removed, facilitating faster and easier application of light during operation. In an embodiment, a sterile cover can also easily sit between the magnetic light source and the endoscope adapter, without damaging the cover and compromising sterility.

In an embodiment, the light source provides narrow-band imaging (NBI) using various LEDs that produce light of varying wavelength in a portable and cost-effective manner. The NBI may be controlled by software run on the smartdevice to optimize imaging quality, instead of through a charge-coupled device. NBI may also be captured and interpreted through the integrated active pixel sensor (APS) of the smartdevice or in conjunction with software run on the smartdevice. In an embodiment, the images captured on the smartdevice may be processed and or enhanced in real time or near real time to provide the user with a greater range of information.

In another embodiment, the endoscope lens is easily aligned with the lens of the smartdevice to improve the direct axis and line of sight between the scope and the smartdevice, this variable axis alignment allows for variations in endoscopes and offers minute adjustment to improve image quality.

In an embodiment, the encasement includes a power supply to power a light source or other peripheral devices. The power source may also power any other attachment, such as a peristaltic pump, that can supply irrigation fluid and air through the endoscope. A suction and/or peristaltic pump can also be utilized to remove debris, fluid, and other bodily mediums. The power supply can also support/charge the smartdevice itself as well as all components within the device, which include microcontrollers, and wireless microcontrollers. The power source may also provide power to the encasement for a communications device, a processor, and other logic and control circuitry.

In another embodiment, the encasement includes a wired or wireless controller mechanism that allows the smartdevice to communicate, either directly or through a network, with the light source and the other peripherals to control their variables (including but not limited to the intensity of light, the wavelength of light to change colors, the rate of inflow/outflow through the peristaltic pump, and the direction of flow). In another embodiment, the smartdevice captures, stores, processes, and transmits images captured locally through an endoscope in both the medical and nonmedical fields.

In another embodiment, an encasement for a smartdevice with a camera is disclosed. The device comprising a mounting mechanism for an endoscope with an eyepiece; a light source; and a power source; wherein the encasement comprises an opening for receiving the smartdevice and the mounting mechanism aligns the eyepiece of the endoscope with the camera of the smartdevice.

In still another embodiment, the encasement comprises a power source with induction charging capability (power transmitted wirelessly across an electromagnetic field). The power source provides power to at least one or all of the following: the smartdevice, the light source, a peristaltic pump, and other modular components. In another embodiment, the encasement comprises a wireless communication interface. In another embodiment, the power source is a battery, which may be rechargeable.

In another embodiment, the encasement comprises a controller, that communications with the smartdevice and controls the light source. In another embodiment, the intensity and wavelength of the light source is controllable by a user from the smart device. In another embodiment, the rate of inflow or outflow through a peristaltic and/or suction pump and the direction of flow of the peristaltic and/or suction pump is controllable by a user.

In an embodiment, an imaging system is disclosed, the imaging system comprising a smartdevice with a camera and a display; a case; an endoscope clamp; a light source; a power source; and a peristaltic and/or suction pump, wherein the endoscope clamp is coupled to the case and aligns an endoscope eyepiece with the camera of the smartdevice such that an image captured by the endoscope is displayed on the smartdevice display.

In another embodiment, the light source may be coupled to the endoscope and the light source and the peristaltic and/or suction pump are powered by the power source.

Other embodiments may include a controller mechanism (hardware or software) that enables the smartdevice to communicate with the light source and the peristaltic pump (for example, adjust brightness level or wavelength of light emitted) and the peristaltic pump (for example, adjust rate of flow or put the pump in reverse to suction fluid out). The invention not only allows the user to visualize the endoscopic image on a screen of the smartdevice (and also transmit, save, process, enhance that image), but also provides its own light source and irrigation solution. The invention differs from current iterations of an attachment device to an endoscopic lens by providing its own light source, power supply, microcontroller with wireless communication abilities, and pump mechanism and serves as an all-in-one mobile and waterproof/sterile platform for endoscopic use in a cost-effective, comprehensive, and safe manner.

The present disclosure utilizes a tablet computer, a smartdevice, such as a smart phone, a micro computer, a laptop, a PDA, or any other device with an optical camera and an internal image processing unit. These devices for example, an iPhone or iPad from Apple® or any Android (Google®) device, are readily available and easy to operate.

The term smartdevice as used herein may refer to an iPad from Apple®, and includes but is not limited to devices with various size displays and processors, such as the iPad Mini, or the iPad Air or any other manufactured smartdevice and/or smart tablet. It may also refer to any other type of tablet type computer or personal device. Additionally, the present disclosure is not limited to any one specific smartdevice type and is adaptable for smartdevices from various manufacturers, such as Apple, Samsung, Microsoft, HTC, Nokia, LG, etc. The smartdevice serves as the image processing center and the display of the smartdevice is used to transmit images from the endoscope to the user. The smartdevice may have one or more camera lenses that may be fixed focal length but may also include smartdevices with more then one camera lens, which may be fixed and or adjustable.

The present disclosure relates to a case or encasement that fits a smartdevice. The encasement may be waterproof, sterile and/or washable and may be made from metal, plastic, rubber, silicone, carbon fiber or any other inert material. The encasement does not cover or interfere with the display of the smartdevice and should not interfere with any of the buttons or the touch screen, and/or other input/output connections. The encasement may have an adjustable mount clamp such as a C-clamp, retainer clip, screw mount, magnetic interface or any other device that will allow the endoscope eyepiece to mate over the camera of the smartdevice. The mount should allow for alignment of the eyepiece on a central axis so that what is viewed through the endoscope can be captured through the lens of the camera of the smartdevice and displayed on the smartdevice screen. The images may also be transmitted from the smartdevice to other networked smartdevices via a wired or wireless connection so that the image may be viewed locally or remotely. In an embodiment, the images are transmitted to a storage device for cataloging and/or post procedure review.

The present embodiment may also include a disposable, removable sterile cover made of plastic or similar type of material that will cover the entire encasement and all connections of the encasement (which includes but is not limited to c-clamp attachments, tubing and light source attachments) to the endoscope. The sterile cover can include specific adapters to bridge the attachments between the c-clamp, tubing, and light source post on the case and the endoscopic instrument. The material of the cover will allow transmission of capacitance and/or pressure to allow for control of touchscreen covered by the cover and not distort images displayed by the screen or transmitted between the endoscope eyepiece and smartdevice camera. This material will also allow for rapid turn around of the encasement system for multiple sterile procedures.

In an embodiment, there may be an adjustable optic such as a lens located on the endoscope, clamp, or encasement that allows for zooming or macro viewing, for example. The adjustable optics may be placed between the encasement and the clamp so that the image captured may be magnified between the endoscope eyepiece and the smartdevice camera. In an embodiment, the optic is incorporated into the encasement. In another embodiment the optic may be a filter or a polarizer. In another embodiment, the encasement comprises a holder for the optic, which may allow for interchanging optical components. In still another embodiment, digital magnification and other digital image processing may also be performed by the smartdevice. The mount also allows for other devices to be placed between the endoscope eyepiece and the smartdevice lens, such as for example, filters or light polarizers.

In an embodiment, a telescopic zoom lens with fixed and variable zoom was used to enlarge the image that was displayed on the smartdevice screen although other types of lenses and magnifications factors may be used. It was found that without some form of additional lens, the transmitted image from the endoscope to the lens of the smartdevice may cause the image to appear as a small circle in the middle of the smartdevice display. This is due to the optics of the endoscope itself, which is designed to be directly viewed through by the eye.

In an embodiment, the device may include a light source, such as but not limited to, a light emitting diode (LED), a laser source, a halogen source, an incandescent source, a fluorescent source at the distal end that attaches to the light guide post of any endoscope to provide illumination at the tip of the endoscope. The light source may be on a retractable cord to facilitate ease of use or maybe incorporated into the endoscope itself. In an embodiment, an LED Emitter Chip may be used. In an embodiment, a LED emitter chip with very high lumens 1000+ that operates at a cool temperature was used. One example of such an LED is the Cree Q5 LED emitter. The reason a high intensity LED is required is because, once the LED connects to the light port of the endoscope, the light is transferred from the base of the endoscope all the way to the tip of the endoscope and there is some loss of light as it travels to the tip of the endoscope where it is projected outward. It will be understood that other forms of illumination standard in the endoscope field may be used without departing from the spirit of the disclosure.

In an embodiment, the device may have an attached or separate adapter such that the light source can be attached to the adapter, either magnetically or screwed on, and the separate or attached light cable of an endoscope can be plugged into the other (receiving) end of the adapter such that the device light source provide light through the light cable of the endoscope.

In an embodiment, the device may also include a peristaltic pump, a suction pump, air pump (to supply oxygen or any type of inhalable gas (in cases of anesthesia), impulse pump, Roots-type supercharger pump, centrifugal pump and/or continuous flow type pump, an irrigation source, that can fit a tubing that channels a liquid or gas medium to flow through the tubing into or out of the endoscope. The pump may be manual or motor driven and can operate in forward or in reverse direction and at variable rates to change the rate of inflow or outflow of the fluid. It will be understood that any forms of pumps such as pumps listed above and/or other standard pumps in the endoscope field may be used without departing from the spirit of the disclosure.

In an embodiment, the encasement may have a separate power supply such as, a battery or transformer. The power source may be a rechargeable battery and may comprise a Nickel Cadmium (NiCd), Nickel Metal Hydride (NiMH), Lithium Ion (Li Ion) and Sealed Lead Acid (SLA) variations (AGM, Gel) battery. The power supply may also be a transformer that converts AC to DC or DC to AC current for use by the various devices and the smartdevice itself. This power supply may power and/or charge the light source, the peristaltic pump, and the smartdevice all of which may have their own power supply. The power source may also be used to power or charge any other device connected to or controlled by the smartdevice or the encasement. The power supply battery may be charged by modalities such as, but not limited to, a wall charger, solar power, another battery, induction charger via wireless electromagnetic fields or a USB connection. In an embodiment, a micro USB Retractable Cable is incorporated into the encasement.

In an embodiment, the battery may be but is not limited to 8000-12000 mAh and may be externally mounted on the encasement. In another embodiment, the battery is incorporated into the encasement, for example, a large flat battery is built into the rear of the encasement adding little bulk to the device.

In an embodiment, a controller mechanism may be incorporated into the encasement that allows the smartdevice or any other device to communicate with and be controlled by or through either direct connection or wirelessly via a short range wireless interface such as for example, Bluetooth, the power supply, the light source, the peristaltic pump and any other devices or features incorporated into the encasement. The controller mechanism may have a user input/interface that is incorporated directly into the case or may be controlled by a software powered user interface in the smartdevice.

In an embodiment, the encasement may include a stabilizing means which may include, but is not limited to, a clamp, an extendable support, a strap, a mounting base, a cuff, a sleeve, or a fold away tripod configuration. In an embodiment, the encasement may include a harness mechanism, in the form of a strap or sleeve which may be fitted to the forearm of the controller to stabilize the device during operation.

In an embodiment, the encasement may not house a smartdevice but may wirelessly communicate to a separate smartdevice or monitor located in proximity to the encasement. In an embodiment, the communications between the encasement and the smartdevice may be accomplished utilizing any short range communications standard or medium.

Utilizing the interface, the user may change and or set different variables and settings of the device, such as, but not limited to, the intensity of light, the wavelength of light to produce a different emitted color by the light source, the rate of inflow/outflow through the peristaltic pump (or any incorporated pump), the direction of the pump motor. The controller may allow for different modes of image capturing and transmission, such as still images, or video, it may allow the user to set resolution, and/or to capture/transmit audio during the procedure. The controller mechanism may also monitor the power supply, pump pressures, memory capacity, fluid levels, etc. and alert the smartdevice as to such things as available battery life, fluid for the pump, available storage, as well as other variables pertinent to the endoscopic procedure.

The interface between the smartdevice and the encasement allows the user to utilize features of the smartdevice to expand the versatility of the endoscopic procedures. For example, the images displayed on the smartdevice may be shared on local or wide area networks, such as the Internet, with other remote users that have access to the network. Utilizing standard or proprietary applications (software) on the smartdevice, a local user may share the endoscopic images with a remote user and/or may communicate via voice or text or other messaging interfaces with other remote users during or after the procedure. Additionally, endoscopic images may be recorded via the smartdevice for transmission to a remote user for educational as well as diagnostic purposes.

The present disclosure may be embodied in the form illustrated in the accompanying drawings. However, attention is called to the fact that the drawings are illustrative. Variations are contemplated as being part of the disclosure, limited only by the scope of the claims

DESCRIPTION OF DRAWINGS

The accompanying drawings illustrate example embodiments of the present disclosure. Such drawings are not to be construed as necessarily limiting the disclosure. Like numbers and/or similar numbering scheme can refer to like and/or similar elements throughout.

FIGS. 9A-9C depict an endoscope clamping mechanism in accordance with an embodiment of the present disclosure.

FIGS. 10A-10D depict an endoscope attachment mechanism in accordance with an embodiment of the present disclosure.

FIGS. 11A-11C depict a light source and magnetic mount in accordance with an embodiment of the present disclosure.

FIGS. 14A-14B depict an embodiment of an encasement with an endoscope attachment that allows for offset viewing in accordance with the present disclosure.

FIG. 15 depicts an embodiment of an encasement that may be worn by a user in accordance with the present disclosure.

DETAILED DESCRIPTION

Figure 1:
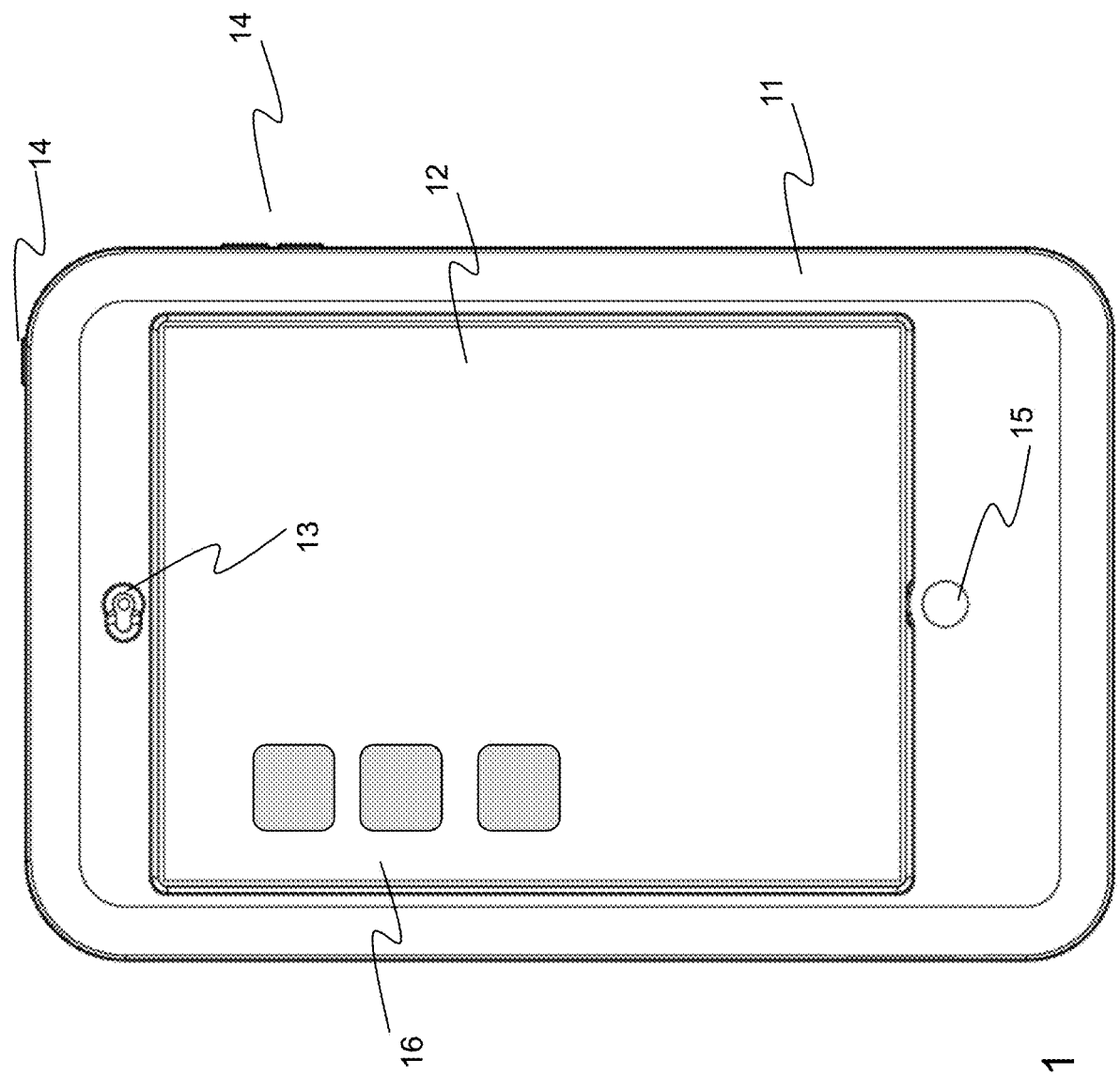
FIG. 1 depicts a front view of an encasement in accordance with an embodiment of the present disclosure.

The present disclosure is now described more fully with reference to the accompanying drawings, in which example embodiments of the present disclosure are shown. The present disclosure may, however, be embodied in many different forms and should not be construed as necessarily being limited to the example embodiments disclosed herein. Rather, these example embodiments are provided so that the present disclosure is thorough and complete, and fully conveys the concepts of the present disclosure to those skilled in the relevant art.

Features described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity in any manner.

The terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

The terminology used herein is for describing particular example embodiments and is not intended to be necessarily limiting of the present disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof.

As used herein, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, a gemstone, an amorphous material, a ceramic, a glass ceramic, an organic solid, such as wood and/or a polymer, such as rubber, a composite material, a semiconductor, a nanomaterial, a biomaterial and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

As used herein, the term "about" and/or "substantially" refers to a +/−10% variation from the nominal value/term. Such variation is always included in any given value/term provided herein, whether or not such variation is specifically referred thereto.

In an embodiment, the encasement is intended to be used in conjunction with a smartdevice such as an iPad tablet. The smartdevice is installed in the encasement and the encasement is sealed. Once secure within the encasement, the smartdevice may be used to view the image captured on an installed endoscope. Specifically, an endoscope may be coupled to the encasement using a clamping mechanism that aligns the endoscope eyepiece with a camera of the smartdevice. The encasement itself contains a power source and the necessary logic to control various accessories including a high intensity light for use with the endoscope. In an embodiment, an accessory attachment is magnetic and allows for coupling of accessories through a magnetic collar screwed onto the endoscope port. In this manner, the installation of accessories, including the high intensity light is quick and easy. The power source within the encasement is used to power the logic in the encasement as well as the accessories coupled to the encasement. Additionally, the power source in the encasement may be inductively charged through the use of a stand or charging station and in turn may charge the installed smartdevice. The encasement is impervious to fluids and can be sterilized so as to be used during medical procedures.

FIG. 1 depicts a front view of encasement 10 in accordance with an embodiment of the present disclosure. Encasement 10 may include a front cover 11, which is configured to protect the installed smartdevice. Encasement 10 may be formed from any type of materials including metal, plastic, rubber, carbon fiber, fiberglass or any combination thereof. Encasement 10 may comprise any material that will be capable of protecting the inserted smartdevice from contamination by fluids. The material for encasement 10 may be such that it can be sterilized using, UV light, heat, autoclave, chemical treatment or any other sterilization procedure that is safe for use during a medical procedure.

In an embodiment, encasement 10 may be molded from two or more sections and have a front portion that covers and protects the display of the smartdevice while allowing for full operation of any form of touch screen on the smartdevice. The front portion or front cover protects the display of the smartdevice and the smartdevice itself from fluid contamination, which may damage either the smartdevice or the display or both. Encasement 10 is configured to allow access to a touch screen, a front facing camera, and various control buttons on the installed smartdevice. Encasement 10 may comprise a touch screen cover 12, front facing camera cover 13, button covers 14 and front control button cover 15. Encasement 10 allows for access to any connectors, adaptors, memory locations, memory devices on the smartdevice without destroying the integrity of the case.

Encasement 10 may have an opening allowing for this insertion of a smartdevice into encasement 10 or it may comprise several parts that when assembled form encasement 10. In an embodiment, encasement 10 may comprise two or more parts that snap, screw, or weld, together or otherwise join together to form a case for the smartdevice. Encasement 10 may have a rear portion (not shown in FIG. 1) that may be permanently attached by chemicals, welding, bonding, one way fasteners, or the like, after a smartdevice is installed. Additionally and/or alternatively, encasement 10 may be separable such that the smartdevice may be removed and/or replaced if necessary.

In an embodiment, encasement 10 may have a flap or hinged cover that ensures that the smartdevice, once inserted will remain within the encasement, but that allows removal of the smartdevice. Additionally, and/or alternatively encasement 10 may have a raised ridge or other stop or latch device that prevents the smartdevice from slipping from the opening once installed. Encasement 10 be made from materials or lined with materials with a high coefficient of friction or may be textured, patterned, or otherwise configured to prevent slippage from the user's grasp. In an embodiment, touch screen cover 12 is sized to allow the user access the entire area of the inserted smartdevice. In another embodiment, the touch screen cover 12 may be partitioned into several regions of various transparencies and/or colors or may be polarized to provide enhanced privacy or viewability. Front facing camera cover 13 may be clear or transparent to the camera of the smartdevice or may be polarized, tinted or otherwise filtered. In an embodiment, the user may use the front facing camera of the smartdevice during the playback of a recorded procedure to video communicate with a user on a remote device. Button covers 14 and 15 are placed to protect and cover the underlying buttons of the smartdevice, while at the same time providing protection to the underlying device. Button covers 14 and 15 may be made of a membrane material such as rubber, latex, plastic, or any other material that is pliable and fluid resistant.

The smartdevice used in conjunction with encasement 10 comprises a processor, a memory and may comprise applications 16. The applications may be instructions to control the encasement 10 and facilitate communications between the encasement 10 and the installed smartdevice. In an embodiment, applications allow communications with a high intensity light and other peripherals that may be coupled to the encasement 10. Additional applications may be used to control different peripherals, edit the captured content, communicate the captured content to a third-party, or store the content on a remote device.

Figure 2:
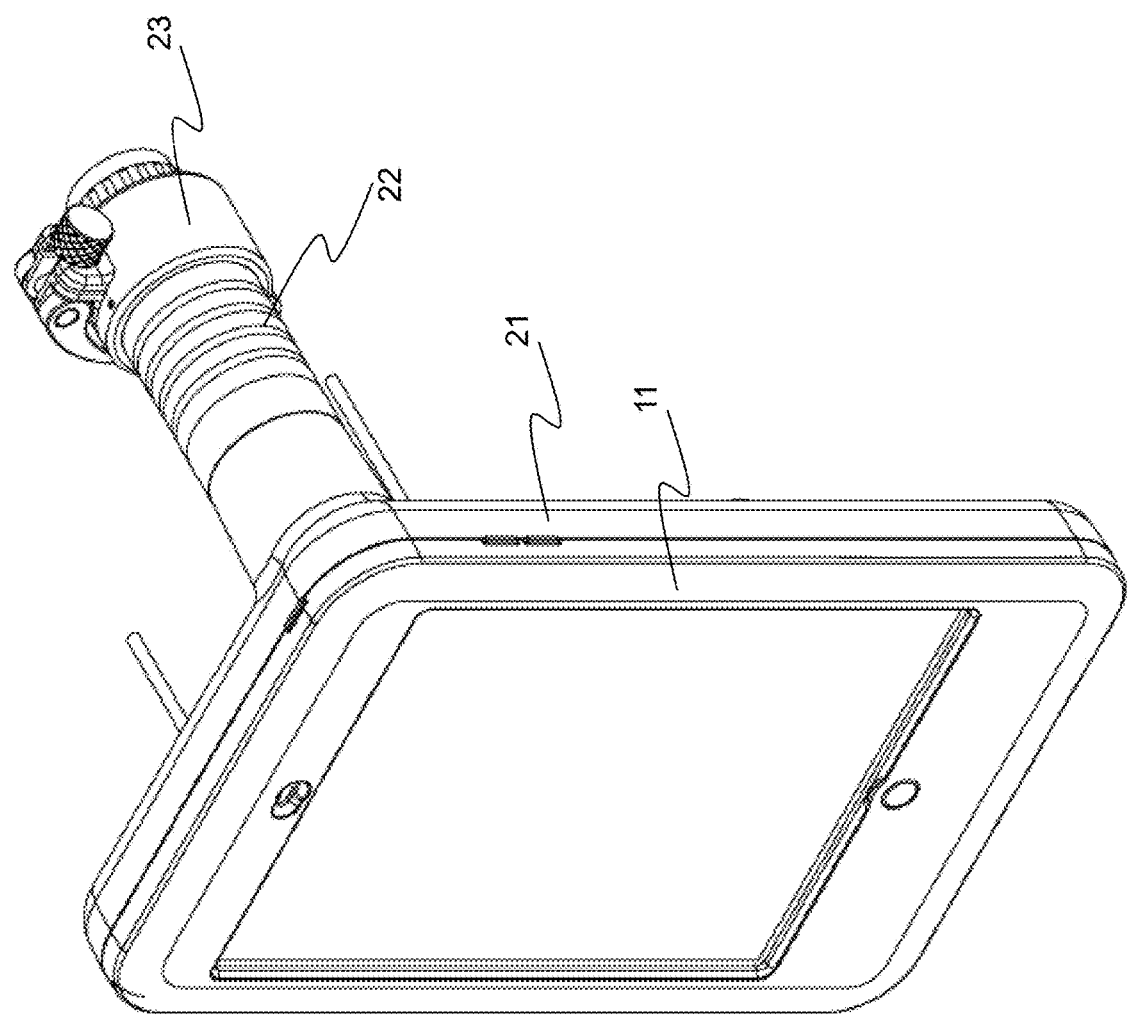
FIG. 2 depicts a perspective view of an encasement with an endoscope support engagement and support mechanism in accordance with an embodiment of the present disclosure.

FIG. 2 depicts a side view of encasement 10 including rear encasement cover portion 21, endoscope attachment 22 and clamp 23. Endoscope attachment 22 aligns with the rear-facing camera of the installed smartdevice. Endoscope attachment 22 may comprise a lens or a series of magnifying lenses. As noted previously, encasement 10 may be comprised of several pieces including front cover 11 and a rear cover 21. Rear cover 21 may be molded as a single piece or as multiple pieces and may be affixed to front cover 11 by any known means. In an embodiment, front cover 11 is permanent affixed to rear cover 21 once a smartdevice is placed between the front and rear covers. Rear cover 21 may be made of plastic, metal, carbon fiber, rubber, glass, or any other material that is impervious to fluids. Rear cover 21 is capable of being sterilized by any known means including heat, chemicals, UV light, etc. endoscope attachment 22 may be permanently affixed to rear cover 21 or may be removeably coupled to rear cover 21. In an embodiment, endoscope attachment 22 and rear cover 21 are molded as a single unit. In an embodiment, endoscope attachment 22 is manufactured from the same materials as rear cover 21. In an alternative embodiment, endoscope attachment 22 is manufactured from a different material as rear cover 21. In an embodiment, endoscope attachment 22 is machined from a single piece of plastic or metal. Endoscope attachment 22 may be threaded or keyed at the proximal end and may screw into a threaded or keyed socket on rear cover 21. Endoscope attachment 22 may be a hollow tube that conveys the image received in the eye piece of the endoscope to the rear facing camera of the smartdevice. Additionally and/or alternatively, endoscope attachment 22 may comprise additional lenses, mirrors, prism, filters, or other optical components to aid and/or assist with focusing the endoscope eyepiece image onto the rear facing camera of the smartdevice.

Clamp 23 is attached to the distal end of endoscope attachment 22 and is intended to receive the eyepiece of a standard endoscope. Clamp 23 may be machined or molded from any suitable rigid material such as metal, plastic, carbon fiber, or the like. Clamp 23 needs to be sufficiently rigid to maintain the positioning of the endoscope with respect to the rear facing camera of the smartdevice in order to convey the endoscope image to the smartdevice. In an embodiment, clamp 23 may comprise a retaining ring, a locking cam lever, a threaded adjustment screw or other locking/clamping mechanisms to secure an endoscope to the endoscope attachment 22. In another embodiment, clamp 23 may comprise an inner portion and an outer portion and may allow the installed endoscope to rotate about a central axis while maintaining its position relative to the rear-facing camera. In an embodiment, the inner portion comprises ball bearing attachments that retain the installed endoscope while allowing it to freely rotate. A rotating mechanism releases the ball bearings into the inner portion where the eyepiece of the endoscope sits. The ball bearings are distributed evenly circumferentially around the eyepiece and clamps the eyepiece in position securely. The ball bearings allow variability in the amount of pressure exerted on the neck (just distal to the eyepiece) of the endoscope, thus applying a varying degree of pressure dependent on the type and width of endoscope neck. The endoscope itself, while secured by the ball bearings in the inner portion of the clamp, can easily rotate along its axis within the clamp facilitated by the ball bearings. The rotating mechanism on the outer portion of the clamp can be released to move the ball bearings from the inner portion back into their neutral position in the outer portion of the clamp, thus releasing the endoscope.

Figure 3:
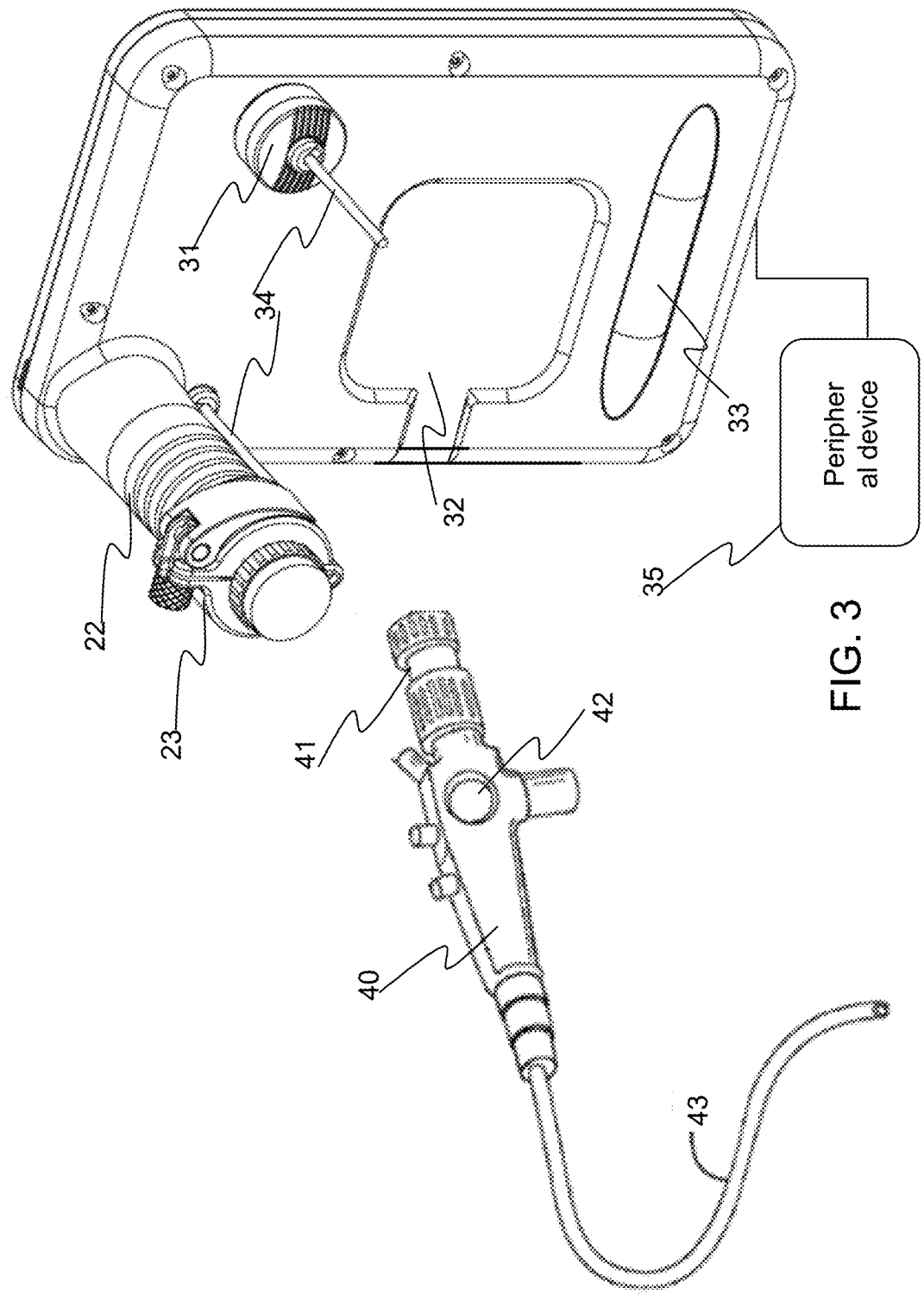
FIG. 3 depicts a rear view of an encasement of the present disclosure, including the endoscope, the endoscope attachment and a light source in accordance with an embodiment of the present disclosure.

FIG. 3 depicts a rear view of encasement 10 and details of an embodiment of rear cover 21. Seen connected to rear cover 21 is endoscope attachment 22 with clamp 23, a high intensity light 31, and a peripheral device 35. Also seen in FIG. 3 is recess 32 which may be molded into rear cover 21, retention ridge 33, endoscope 40 with eyepiece 41, light port 42 and flexible shaft 43. In an embodiment, endoscope 40 may be secured to endoscope attachment 22 using clamp 23. In an embodiment, claim 23 may be sized to securely retain endoscope 40 by clamping onto eyepiece 41. It may be a single clamp, double clamp or a series of independent but interconnected clamps. It will be understood by those skilled in the art that clamp 23 may be adjusted and or modified to account for the various different eyepieces found on endoscopes without departing from the spirit of the present disclosure.

High intensity lamp 31 is connected to encasement 10 via cable 34. Cable 34 may be permanently attached to rear cover 21 or may be retractable, removable, or otherwise disengageable from encasement 10 for storage, cleaning and sterilizing purposes. Cable 34 couples high intensity light 31 to a power source in encasement 10. High intensity lamp 31 may be coupled to endoscope 40 via light port 42 to provide illumination at the distal end of flexible shaft 43. As will be discussed more fully with respect to FIGS. 9A-9C, high intensity lamp 31 may couple to endoscope 40 via, mechanical or magnetic connection.

Peripheral device 35 may couple to encasement 35 through connector 56 and may be permanently coupled or removable. It may also be coupled to encasement 10 via an additional connector or connection. Peripheral device 35 may be a peristaltic pump, irrigation device, audio capturing device, or any other accessory or peripheral device used in conjunction with an endoscope. It may be powered directly by the power source of encasement 10 or may comprise its own power source. Peripheral device 35 may be directly controlled via wired or wireless connection by the smartdevice or via its coupling to encasement 10.

Recess 32 may be any shape and is a molded area in the rear cover 21. Recess 32 may be shaped to retain encasement 10 on a stand or charging station and may be located so as to contact a charging station to charge the installed smartdevice and/or encasement power supply. Recess 32 may be flat as well as protruding and may provide other connections to a charging station as well. Recess 32 may have male or female connectors that engage or otherwise mate with corresponding connectors on a charging or mounting station. Recess 32 may be positioned to be directly align an induction coil 4 in the encasement adjacent to an induction coil in the charging station when placed in the charging station 90.

Retention ridge 33 may be sized and shaped to mate with a corresponding size and shape on a charger or stand and may be either convex or concave. Retention ridge 33 may be combined with recess 32 or may be separate. As will be understood, other methods and geometries may be used to retain encasement 10 on a stand or charging station with out departing from the present disclosure. Retention ridge 33 may be a lip, a ridge, a recess, or a press fit. Retention ridge 33 may also be an area of high viscosity and/or adhesion that prevents encasement 10 from sliding from a mounting or charging station. Retention ridge 33 may be rubber, silicone, plastic, or any other high viscosity material. It will further be appreciated, that retention ridge 33 may comprise a magnet or an area of magnetic metal.

When storing encasement 10, in accordance with an embodiment of the present disclosure, encasement 10, with a smartdevice installed may be placed on a charging station or stand 90 and recess 32 may mate or otherwise contact charging area 92 and retention recess may mate or otherwise contact retention area 93. In this manner, when encasement 10 is placed on stand 90, it will remain in position without slipping or otherwise sliding from the stand 90.

Figure 4B:
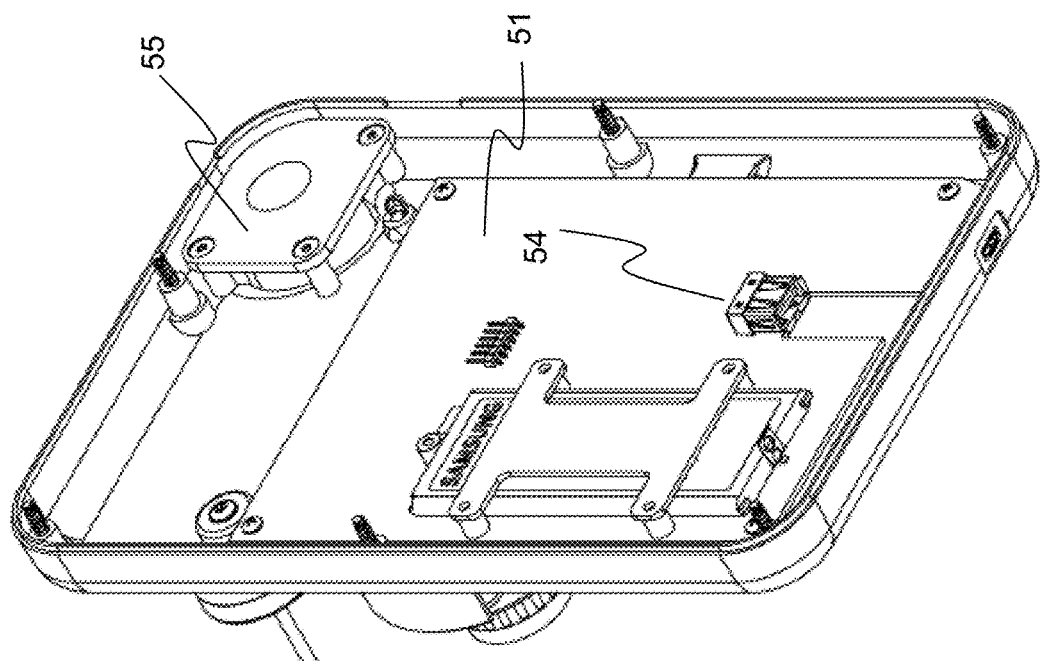
FIGS. 4A-4B depict internal views of the rear portion of an encasement in accordance with an embodiment of the present disclosure.
Figure 4A:
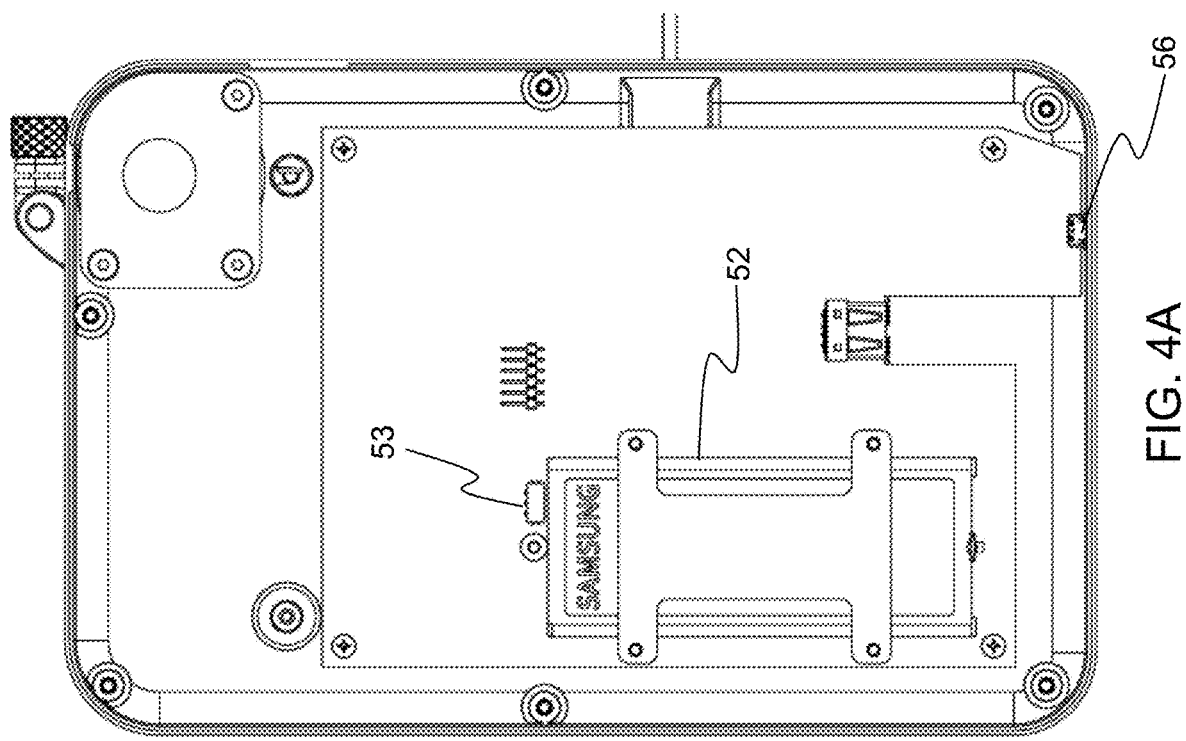

FIGS. 4A and 4B depict the interior portions of rear encasement portion 21. Located internal to encasement 10 is circuit board 51, battery 52, communications circuit 53, connector 54, endoscope attachment mount 55, and connector 56. Circuit board 51 may be a single layer board or a multilayer board. Circuit board 51 may comprise both active and passive components and may be a single board or multiple boards. Circuit board 51 may contain electronics to control power regulation, power selection, charging of battery 52, induction circuitry, communications circuitry, logic circuitry to control the high intensity light 31, logic to detect fault conditions, logic circuitry to control other peripheral devices. Circuit board 51 may have connectors, such as connector 56 mounted directly to the board. In an embodiment, connector 56 is an external power connector that may be used to power encasement 10, charge battery 52, power connected peripherals, or high intensity light 31. Additionally, and/or alternatively, connector 56 may be a data connector that controls circuit board 51 or communications between encasement 10 and an external device. Connector 56 may be used to troubleshoot or program any device or update firmware on circuit board 51. Additionally, and/or alternatively, connector 56 may be connected to a peripheral device, such as a peristaltic pump, suction, irrigation, gas insufflator, or personal computer. Circuit board 51 may comprise a processor, memory, I/O power modulation, power control, communications modules, and any other electronic component.

Battery 52 may be electrically coupled to circuit board 51 and may be mounted on circuit board 51, although it may be mounted separately as well. Battery 52 may be a power source, and may be rechargeable, replaceable, or disposable. Battery 52 may be made from a variety of materials, such as AgZn, Lithium ion, NiCd, NiMH, NiZn, Alkaline, Lithium, Magnesium, Mercury oxide, Nickel oxyhydroxide, Silver-oxide (silver-zinc), Zinc-air, Zinc-carbon, Zinc-chloride. Battery 51 may provide power to circuit board 51 as well as high intensity light 31 and any other attached peripheral device. Battery 52 is of sufficient capacity and voltage to ensure illumination of high intensity light 31 during a procedure as well as powering other peripherals when necessary. Battery 52 is capable of cycling (i.e., charging and discharging) many times.

Communications circuit 53 may be mounted directly on circuit board 51 or may be mounted as a separate module. Communications circuit 53 may be any short range communications module that communicates with the installed smartdevice. Communications circuit 53 communicates via a short range communications protocol, such as Bluetooth™, although other protocols are acceptable. Other protocols include but are not limited to low energy Bluetooth (BLE), ZigBee, Ru-Bee, Wi-Fi, infrared, or mobile data such as 3G/4G. Communications circuit 53 communicates both to and from encasement 10 to the installed smartdevice, or to any other wireless transceiver capable of receiving and transmitting close range communications. Communications circuit 53 handles communications to/from the installed smartdevice and the encasement 10. In operation communications module 53 may receive commands from the smartdevice to control the high intensity light 31 or any other attached peripherals. It may also communicate information to the smartdevice, such as available battery life, fault conditions, or the status of peripheral devices.

In operations, a client 16 or application may be installed on the smartdevice that controls the communications with the encasement 10. Installation may include a wired or wireless installation and may be delivered in any suitable format. The client 16 may be available on-line from the vendor or may be download from an AppStore such as the Apple® store or Google Play®. Once installed, the user of the encasement may control the encasement using standard smartdevice interfaces and commands.

Connector 54 is a board mounted connector that mates directly to the installed smartdevice. It may be a USB connector, micro USB connector, an edge connector or any other type of connector with any number of pins or connections. When a smartdevice is installed, such as an Apple® iPad, iPhone, Android based tablet or phone, it may be powered and or charged directly through connector 54. Similarly, communications directly to the installed smartdevice may be possible via connector 54. Connector 54 may interface with any edge or the smartdevice and may connect to the smartdevice directly or through a cable or other extender connector.

In operation, when a smartdevice is installed within encasement 10, it is coupled to circuit board 51 via connector 56. When encasement 10 is placed on charging station 90, battery 52 is inductively charged via induction and power circuitry located in power station 90 and circuit board 51. Similarly, the smartdevice is charged via the induction circuitry through connector 56. In this manner, neither the smartdevice nor the encasement needs to be directly connected to a power source to keep the devices charged. The induction circuitry may be consist of both a transmitting coil and receiving coil. The transmitting coil maybe located within the charging stand or on top of the charging stand. The receiving coil is located on the main circuitry board or anywhere else within the encasement as to allow transmission to and from a transmitting coil through the encasement.

Figure 5:
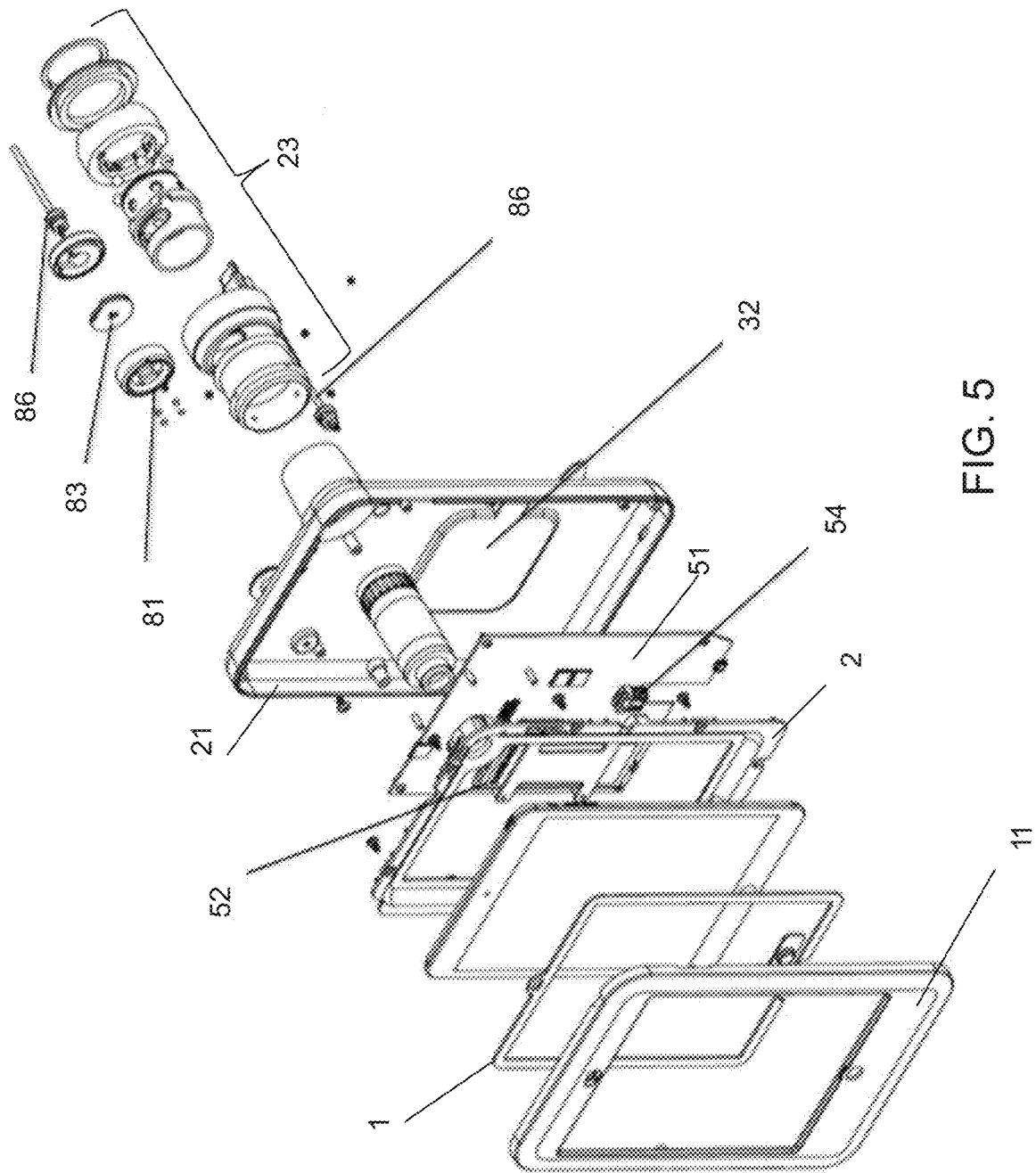
FIG. 5 is an exploded view of encasement 10 from the front side with an inserted smartdevice in accordance with an embodiment of the present disclosure.

FIG. 5 is an exploded view of encasement 10 from the front side with an inserted smartdevice. Encasement 10 includes front cover or exterior shell 11, frame or gasket 1, securement plate 2, circuit board 51, and exterior shell or rear encasement cover portion 21. Also depicted is an embodiment of clamp 23, portions of high intensity lamp 31, including housing 81, LED board 83 and power cord 86. Frame or gasket 1 may be foam, metal rubber, silicon, or plastic and is intended to cushion the installed smart device when installed within encasement 10. Frame or gasket 1 may also include a cover that overlays the smartdevice touch screen. Securement plate 2 is form fitted to retain the smartdevice and may be a frame that when combined with the front-cover 11 sandwiches in the smart device retaining it in a secure position.

Figure 6:
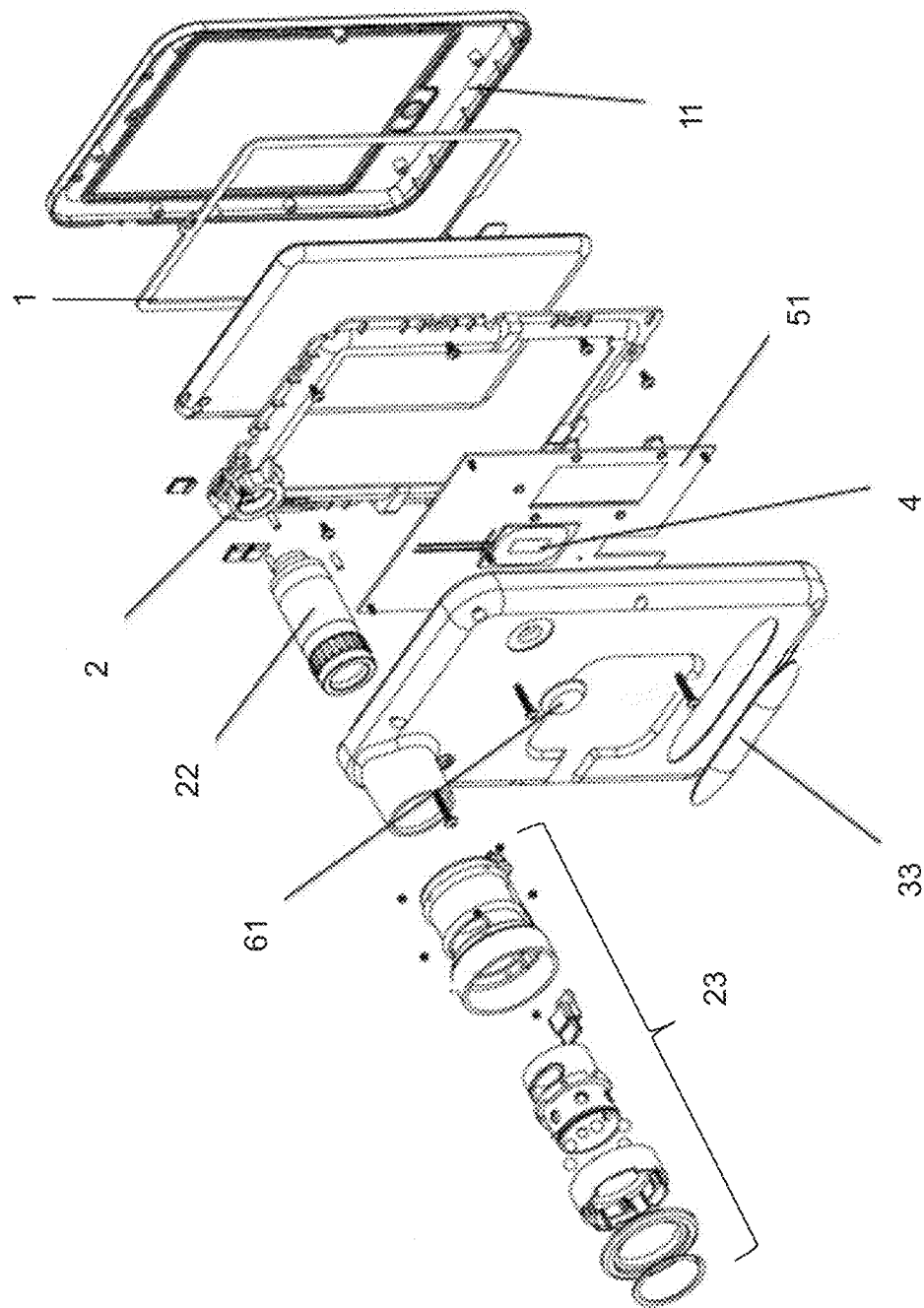
FIG. 6 is an exploded view of encasement 10 from the rear side with an inserted smartdevice in accordance with an embodiment of the present disclosure.

FIG. 6 is an exploded view of encasement 10 from the rear side with an inserted smart device. As seen in FIG. 6, the rear side of circuit board 51 may comprise the induction coil 4 for wireless charging. In an embodiment, the charging station 90 compromises a second induction coil, and the encasement utilizes an electromagnetic field to transfer energy between two objects. Energy is sent through the inductive coupling created between charging station 90 and induction coil 4 to aid with charging battery 52 and the encasement 10 as well as the smart device. As is know, the induction charging use the induction coil in charging station 90 to create an electromagnetic field and induction coil 4 in the encasement utilizes the power from the electromagnetic field and converts it back into electrical current to charge battery 52. The two induction coils in proximity combine to form the electrical transformer.

Also seen in FIG. 6 is high intensity lamp attachment 61. High intensity lamp attachment 61 may be a magnetic metal or may be a magnet itself. It is sized and shaped to correspond to high intensity lamp 31 and may be integrated into rear cover 21 or may be surface mounted on rear cover 21. High intensity lamp attachment 61 provides a docking station for high intensity lamp 31 when in a stowed position.

Figure 7:
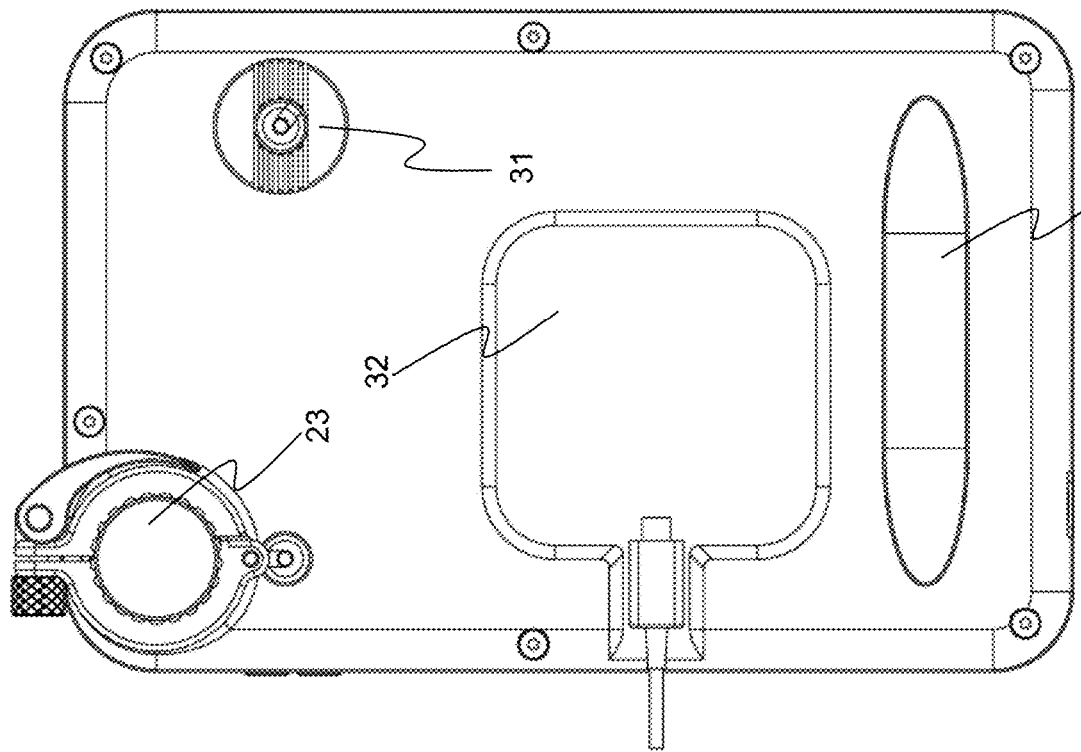
FIG. 7 depicts a rear view of an encasement in accordance with an embodiment of the present disclosure.

FIG. 7 depicts a rear view of encasement 10. High intensity lamp 31 is seen in a stored position on the rear of the encasement. Also shown are recess 32, ridge 33 and clamp 23.

Figure 8:
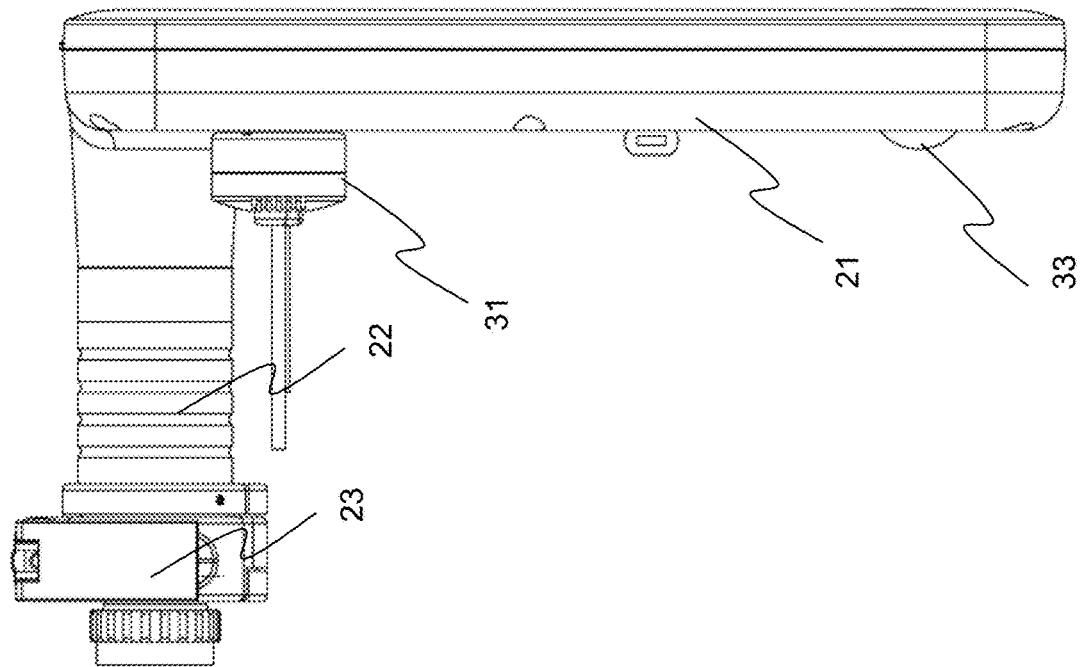
FIG. 8 depicts a side view of an encasement of the present system including the light source and endoscope mount in accordance with an embodiment of the present disclosure.

FIG. 8 depicts a side view of encasement 10 with high intensity light 31 in a stowed position. As will be appreciated by those skilled in the art, encasement 10 and all the required attachments and connectors may be stored on the encasement. In this manner, it is self contained, hand held, portable and easy to operate.

FIG. 9 depicts clamp 23. Clamp 23 quickly and easily locks endoscope 40 in place with respect to the endoscope attachment 22. Utilizing clamp 23, the encasement 10 is able to bear the weight and torque of the attached endoscope. Clamp 23 comprises a thumb screw 71, cam arm 72, collars 73 and 74, pivot pin 75 and latch 76. In operation, clamp 23 is opened by lifting cam arm 72 away from collar 73. This releases thumb screw 71 from latch 76. Once thumb screw 71 clears latch 76, collars 73 and 74 pivot about pivot pin 75 allowing clamp 23 to be opened. Once in an open position collars 73 and 74 are placed around the neck of eyepiece 41 of endoscope 40. To clamp the endoscope in place, collars 73 and 74 are brought together, thumb screw 71 is inserted into latch 76 and cam arm 72 is closed. Thumb screw 71 may be adjusted to ensure a proper fit around the neck of eyepiece 41. In this manner, the endoscope 40 is quickly and easily positioned and aligned with the endoscope attachment 22 and the underlying smartdevice camera. When the smartdevice is powered on and the rear camera enabled, the image conveyed to eyepiece 41 of endoscope 40 will be viewable on the display of the smartdevice within area 12.

With an image displayed, the functionality of the smartdevice may be employed to capture still images, record videos, transmit videos, annotate and otherwise edit the incoming images. Images may be transmitted to additional displays through the wireless connection of the smartdevice or may be stored simultaneously to a secure server or a remote or local storage device such as a public or private cloud. Images may be shared live or from stored images via any supported teleconferencing or telemedicine technology.

FIGS. 10A-10D depict an embodiment where clamp 23 comprises comprise an inner portion 100 and an outer portion 102 and may allow the installed endoscope to rotate about a central axis while maintaining its position relative to the rear-facing camera. In an embodiment, the inner portion 100 comprises ball bearings 104 that retain the installed endoscope while allowing it to freely rotate. A rotating mechanism 106 releases the ball bearings 104 into the inner portion 100 where the eyepiece of the endoscope sits. The ball bearings 104 are distributed evenly circumferentially around the eyepiece and clamps the eyepiece in position securely. The ball bearings 104 allow variability in the amount of pressure exerted on the neck (just distal to the eyepiece) of the endoscope, thus applying a varying degree of pressure dependent on the type and width of endoscope neck. The endoscope itself, while secured by the ball bearings 104 in the inner portion 100 of the clamp, can easily rotate along its axis within the clamp facilitated by the ball bearings 104. The rotating mechanism 106 on the outer portion 102 of the clamp can be released to move the ball bearings 104 from the inner portion 100 back into their neutral position in the outer portion 102 of clamp 23, thus releasing the endoscope.

FIGS. 11A and 11B depict high intensity light 31. High intensity light 31 comprises housing 81, LEDs 82a-82n, LED board 83, lens 84, mounting ring 85 and power cable 86. High intensity light 31 is a high intensity light that connects to endoscope 40 at light port 42 and conveys light down the flexible shaft of the endoscope to the distal end to illuminate the area being examined. High intensity light 31 may screw into port 42 or may connect by any other known method, including, press fit, magnetic, etc. In an embodiment, a magnetic coupler 87 may be used. Hosing 81 may be made from metal, plastic, carbon fiber, or any other suitable materials and may be machined or molded. Housing 81 may be a single piece or may be multiple pieces and may be round or any other geometric shape. Housing 81 should be sized sufficiently to house an illumination source. LED board 83 may be a single or multi layer circuit board and comprises the necessary circuitry to drive LEDs 82a-n. it may comprise solid state devices as well as individual components. It is sized and shaped to fit within housing 81. Power cable 85 is coupled to the back of housing 81 on one end and may be connected directly to the encasement through a power port or may be removable connected to the encasement, through for example connector 56. In an embodiment, power cable 85 was retractable into housing 81.

In an embodiment, the illumination sources include high intensity bulbs, high-intensity discharge bulbs, LEDs, halogen bulbs. In an embodiment, three LEDs were used although more or less may be used. In an embodiment, a white LED, a blue LED and a green LED were used as illumination sources. The multiple LEDs may be used separately or in combination. For example, in an embodiment, the white LED may be used for general illumination and the green and blue LED may be used for narrow band imaging. Narrow band imaging as explained in U.S. Pat. No. 8,979,741 to Igarashi, et al., which is incorporated by reference in its entirety, allows for image enhancement that improves the visibility of blood vessels and other structures under examination. Utilizing two LEDs the narrow band imaging light is composed of just two specific wavelengths that may be strongly absorbed by hemoglobin or other internal organs. The shorter blue wavelength may only penetrates the superficial layers of the mucosa, while the longer green wavelength light may penetrates deeper.

In an embodiment, a blue LED in the 405 to 600 nm range may be used with a blue LED in the range of 520 to 560 preferred. In an embodiment, a green LED in the 600 to 700 nm range may be used with a green LED in the range of 630 to 670 preferred.

Lens 84 covers and protects the LEDs 82a-82n and may be flush mounted, or recessed within mounting ring 85. Lens 84 may be glass, plastic, sapphire, or any other transparent material. Lens 84 may be sealed to mounting ring 85 using mechanical or chemical bonding and creates a fluid impermeable seal thereby protecting LEDs 82a-82n. In an embodiment, lens 84 may be tinted, filtered, or otherwise modified to prohibit and/or modify certain frequencies of light from passing through. In an embodiment, mounting ring 85 is comprised of a material susceptible to magnetic force.

FIG. 11C depicts a connector for use with an embodiment of the present disclosure. Accessory connector 87 comprises insertion portion 88 and mounting portion 89. Insertion portion 88 is configured to mate with an endoscope light port 42 and may be threaded or otherwise milled, keyed or shaped to engage with a standard endoscope light port. In an embodiment, insertion portion 88 was threaded. In an embodiment, mounting portion 89 is configured to allow connection to mounting ring 85. In an embodiment, mounting portion 89 is magnetic and mounting ring 85 comprises a metal that is either magnetic or susceptible to magnetic force.

In an embodiment, during operation, accessory coupler 87 is screwed into light port 42. Once installed, high intensity light 31 may be easily and quickly coupled or decoupled from the accessory coupler 87 using the magnetic connector. In this way a quick and easy connection or disconnection may be accomplished and the need for portable light source is eliminated. Further, other accessories may be coupled to the endoscope using magnetic coupler in various endoscope ports.

Figure 12:
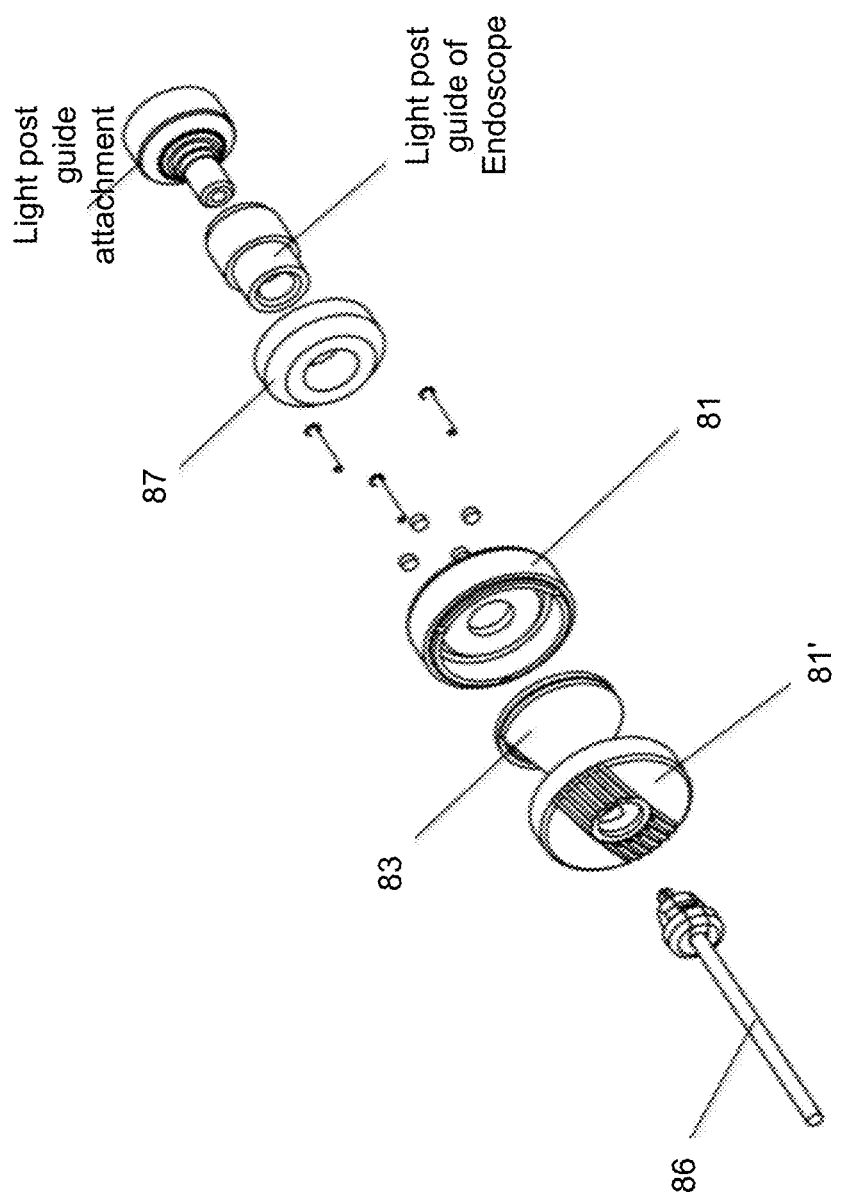
FIG. 12 is an exploded view of a high intensity lamp in an embodiment of the present disclosure.

FIG. 12 depicts an exploded view of high intensity lamp 31. High intensity light 31 comprises housing 81, housing outer shell 81', LED board 83, power cable 86. Also shown is magnetic coupler 87 and the light post guide and light post guide attachment for a typical endoscope.

Figure 13:
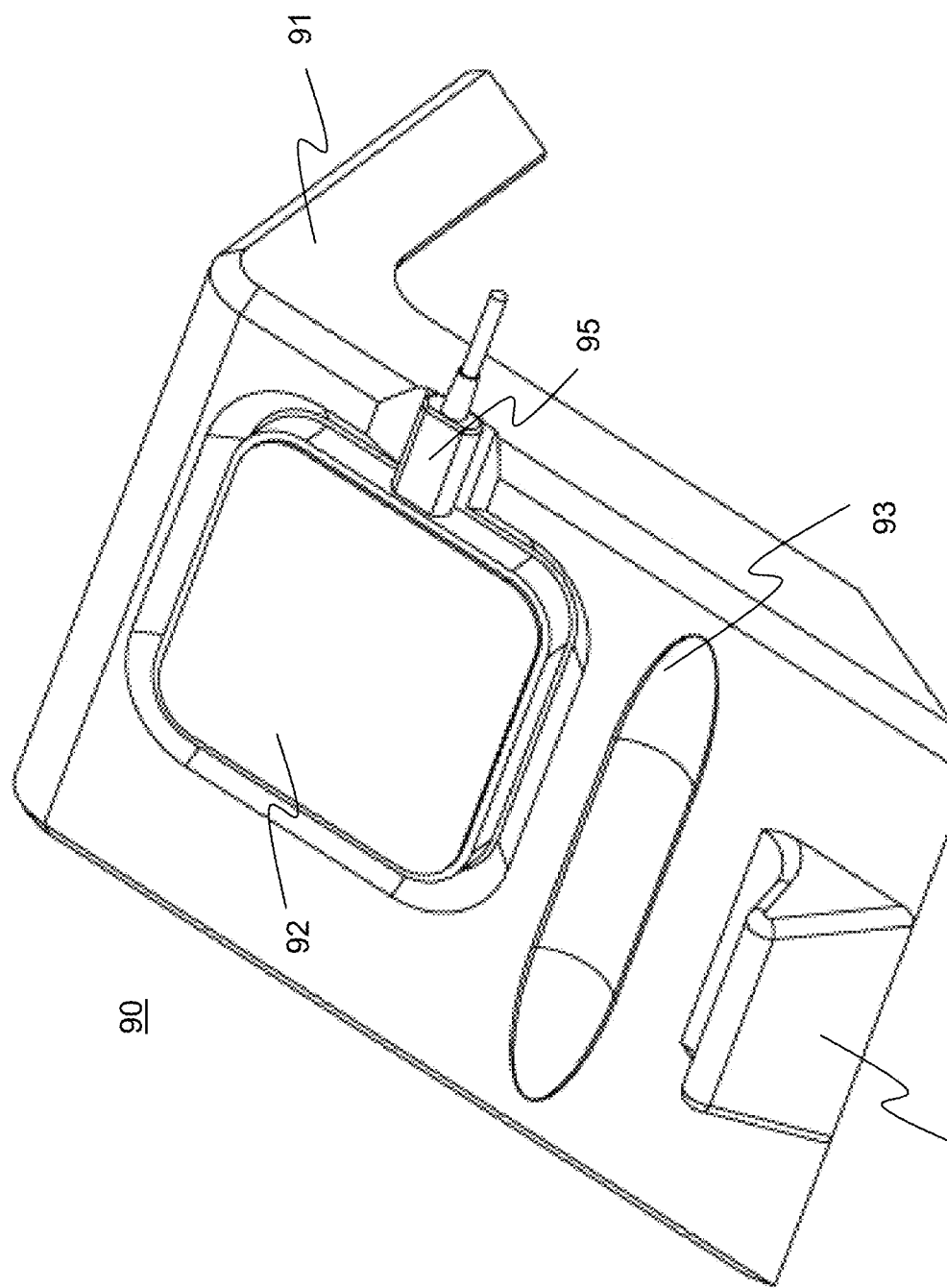
FIG. 13 depicts a charging station for the encasement in accordance with an embodiment of the present disclosure.

FIG. 13 depicts charging station or stand 90. Charging station 90 comprises stand 91, contact charging area 92, retention area 93, ledge 94 and power connector 95. Charging station 90 is used to charge the encasement, charge the smartdevice, and store the encasement. Stand 91 may be manufactured from metal, plastic, wood or any other suitable material. It is high enough to ensure that when the encasement is resting in the stand, endoscope attachment 22 does not contact the underlying surface. Contact charging area 92 protrudes from the surface of stand 90 and is shared to mate with recess 32 on the rear of encasement 10. Contact charging area 92 comprises internal circuitry and may include an induction coil, a transformer an AC to DC converter or any other circuitry, to inductively charge battery 52 when encasement 10 is resting on the stand. Contact charging are 92 may similarly be recessed and recess area 32 may extend from the rear of encasement 10. Contact charging are 92 can be any size, and shape and should match the size and shape of recess 32 and allow recess 32 to rest in close proximity to contact charging area 92 when encasement 10 is on the stand.

Retention area 93 is a means of mechanical retention for encasement 10 and aids with the alignment of encasement 10 when it is at rest on charging station 90. It may be any geometric shape and may be molded into stand 91 or may be an additional attachment. In an embodiment, retention area 93 was shaped to conform to retention ridge 33. Ledge 94 engages the lower edge of the encasement 10 when it is resting on the stand and should be sufficiently concave or otherwise shaped to aid in the retention of encasement 10. A power connector 95 may be coupled to charging station 90 via a connector or may be hard wired into charging station 90. Power connector 95 may connect directly to contact charging area 92 or may couple to contact charging area 92 via a separate connector (not shown) on the charging station 90.

In an embodiment, in operation, one end of power connector 95 may be connected to an AC power source or to a DC source such as through a USB connector. If connected to an AC source, a transformer may be necessary to ensure that the correct voltage is delivered to contact charging area 92. Contact charging area 92 comprises an induction coil and may operate between at 0 to 25 volts DC and preferable in the +5 volt range. Contact charging area 92 comprise the necessary induction charging circuitry to charge the encasement when it is resting in the charging stand 90. In this manner, encasement 10 and the installed smartdevice will remain in a charged condition and will be ready to be used by an operator when required. Additionally, encasement 10 does not require connection via any cables to operate thereby greatly improving the portability and the maneuverability of the device.

FIGS. 14A and 14B depict an embodiment that allows endoscope 40 to be rotated relative to encasement 10. As seen in FIG. 14A rotating hub 140 may be coupled to endoscope attachment 22. Hub 140 may comprise two or more sections or segments that mount onto endoscope attachment 22 or may be integrated directly into endoscope attachment 22. The endoscope attachment 22 and hub 140 may be rotated and stored in a neutral position as seen in FIG. 14A, at which point the mirror 141 in hub 140 enters a parallel orientation to the lens and does not obstruct the direct image 143 transmitted from the endoscope 40 to the lens of the smartdevice.

FIG. 14B depicts hub 140 at a rotated angle, such that encasement 10 lies at a ninety degree angle relative to endoscope 40. It is to be understood that the angle of rotation may be from zero degrees to ninety degrees. Hub 140 comprises reflective mirror 141 that allows the image 143 from endoscope 40 to be magnified or otherwise manipulated and then transmitted through the angle of rotation onto the lens of the smartdevice camera. In addition to reflective mirror, additional optics, such as prisms, lenses, filters, polarizers or any other optical component may be included within hub 140 and/or endoscope attachment 22 to compensate, magnify filter or otherwise manipulate image 143 prior to striking the lens of the camera of the installed smart device.

FIG. 15 depicts an embodiment with a lanyard or harness 150 attached to encasement 10 through a hook or clamp mechanisms 151. The lanyard or harness 150 can be worn by a user on the body either around the user's neck, shoulder, arm, or torso to redistribute the weight of the encasement 10 to the body of the user. The lanyard or harness 150 may improve ergonomics of the encasement during use and provide stability during operation. Lanyard or harness 150 may be capable of being sterilized or may be disposable. It may be made of natural or man made fibers, plastic or rubber. It may be coated and may have additional openings or connectors to size and stabilize the encasement 10 when it is in use by a user. Hook 151 may be any type of clamp, hook, latch, or other mechanism to connect lanyard or harness 150 to encasement 10.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration provided herein is by way of example, and the scope of the application is not limited to the exact details shown or described.

Although the foregoing detailed description has been described by reference to a number of exemplary embodiments, it will be understood that certain changes, modification or variations may be made in embodying the above application, and in the construction thereof, other than those specifically set forth herein, may be achieved by those skilled in the art without departing from the spirit and scope of the application, and that such changes, modification or variations are to be considered as being within the overall scope of the present application. Therefore, it is contemplated to cover the present application and any and all changes, modifications, variations, or equivalents that fall within the true spirit and scope of the underlying principles disclosed and claimed herein. Consequently, the scope of the present application is intended to be limited only by the attached claims, all matter contained in the above description and shown in the accompanying drawings shall be interpreted as illustrative and not in a limiting sense.

What is claimed is:

1. A device comprising:
a case including a rear cover, wherein the rear cover hosts a circuit board, a light source, and a battery, wherein the circuit board is coupled to the battery, wherein the light source is coupled to the battery, wherein the rear cover includes an inner side and an outer side, wherein the inner side hosts the circuit board and the battery, wherein the outer side hosts the light source, wherein the light source includes a high intensity lamp that is configured to be powered by the battery and thereby output a light into an endoscope when the light source is coupled to the endoscope such that the endoscope can be used to inspect a cavity via the light, wherein the high intensity lamp is not co-aligned with a camera of a smart device when the case encases the smart device and the camera co-aligns with the endoscope.

2. The device of claim 1, wherein the outer side has a tube extending therefrom, wherein the tube contains a lens, wherein the lens is co-aligned with the camera of the smart device when the case encases the smart device and the high intensity lamp is coupled to the endoscope such that the endoscope can be used to inspect the cavity via the light.

3. The device of claim 2, wherein the tube hosts a clamp distal to the rear cover.

4. The device of claim 1, wherein the rear cover hosts a short range wireless communications circuit coupled to the circuit board, wherein the short range wireless communications circuit is configured to wirelessly communicate with the smart device when the case encases the smart device such that the high intensity lamp is controllable from the smart device.

5. The device of claim 4, wherein the short range wireless communications circuit is configured to be powered by the battery.

6. The device of claim 1, wherein the rear cover hosts a connector coupled to the circuit board.

7. The device of claim 6, wherein the connector is mounted to the circuit board.

8. The device of claim 6, wherein the connector enables the battery to be recharged when the connector connects with a power source.

9. The device of claim 6, wherein the connector enables the circuit board to send or receive data therethrough when the connector connects with a data source.

10. The device of claim 6, wherein the connector connects to at least one of a peristaltic pump, a suction device, an irrigation device, a cauterizer, an insufflator, a gas delivery device, a gas insufflator, a vital measurement device, or a fluid management system when the light source is coupled to the endoscope such that the endoscope can be used to inspect the cavity via the light.

11. The device of claim 10, wherein the connector enables the smart device to control the at least one of the peristaltic pump, the suction device, the irrigation device, the cauterizer, the insufflator, the gas delivery device, the gas insufflator, the vital measurement device, or the fluid management system when the case encases the smart device and the light source is coupled to the endoscope such that the endoscope can be used to inspect the cavity via the light.

12. The device of claim 6, wherein the connector mates with the smart device when the case encases the smart device such that the connector enables at least one of the battery charging the smart device or the circuit board communicably interfacing with the smart device.

13. The device of claim 1, wherein the circuit board enables wireless charging of the smart device when the case encases the smart device.

14. The device of claim 1, wherein the circuit board enables wireless charging of the battery.

15. The device of claim 1, wherein the case includes a front cover, wherein the front cover and the rear cover are a single unitary molded piece.

16. The device of claim 1, wherein the circuit board is configured to control the light source including the high intensity lamp when the light source is coupled to the endoscope such that the endoscope can be used to inspect the cavity via the light.

17. A device comprising:
a case including a rear cover, wherein the rear cover hosts a short range wireless communications circuit, a light source, and a battery, wherein the short range wireless communications circuit is coupled to the battery, wherein the light source is coupled to the battery, wherein the rear cover includes an inner side and an outer side, wherein the inner side hosts the short range wireless communications circuit and the battery, wherein the outer side hosts the light source, wherein the short range wireless communications circuit is configured to wirelessly communicate with a smart device having a camera when the case encases the smart device such that (i) the light source is controllable from the smart device, (ii) the light source is not co-aligned with the camera, and (iii) the camera co-aligns with an endoscope coupled to the light source for the endoscope to be used to inspect a cavity based on the light source.

18. The device of claim 17, wherein the outer side has a tube extending therefrom, wherein the tube contains a lens, wherein the lens is co-aligned with the camera when the case encases the smart device.

19. The device of claim 18, wherein the tube hosts a clamp distal to the rear cover.

20. The device of claim 17, wherein the rear cover enables wireless charging of the battery.

* * * * *